US010028724B2

(12) United States Patent
Honjo et al.

(10) Patent No.: US 10,028,724 B2
(45) Date of Patent: Jul. 24, 2018

(54) ULTRASONIC DIAGNOSIS APPARATUS AND IMAGE PROCESSING METHOD

(71) Applicant: Toshiba Medical Systems Corporation, Otawara-shi (JP)

(72) Inventors: Yasunori Honjo, Otawara (JP); Yasuhiko Abe, Otawara (JP); Tetsuya Kawagishi, Nasushiobara (JP); Makoto Hirama, Otawara (JP); Takeshi Sato, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 638 days.

(21) Appl. No.: 14/612,458

(22) Filed: Feb. 3, 2015

(65) Prior Publication Data

US 2015/0223778 A1    Aug. 13, 2015

(30) Foreign Application Priority Data

Feb. 10, 2014    (JP) .................................. 2014-023624

(51) Int. Cl.
*A61B 8/14* (2006.01)
*A61B 8/08* (2006.01)
(Continued)

(52) U.S. Cl.
CPC .............. *A61B 8/14* (2013.01); *A61B 8/0858* (2013.01); *A61B 8/4488* (2013.01);
(Continued)

(58) Field of Classification Search
CPC ....... A61B 8/0858; A61B 8/5269; A61B 8/14; A61B 8/4488; A61B 8/54; A61B 8/5207;
(Continued)

(56) References Cited

U.S. PATENT DOCUMENTS 4,242,912 A * 1/1981 Burckhardt .............. A61B 8/14
310/334
5,421,333 A * 6/1995 Takamizawa ....... G01S 7/52046
600/447

FOREIGN PATENT DOCUMENTS

EP    1 439 402 A1    7/2004

OTHER PUBLICATIONS

U.S. Appl. No. 14/709,628, filed May 12, 2015, Honjo, et al.
Extended European Search Report dated Jul. 13, 2015 in Patent Application No. 15154355.0.

* cited by examiner

*Primary Examiner* — Bo J Peng
(74) *Attorney, Agent, or Firm* — Oblon, McClelland, Maier & Neustadt, L.L.P.

(57) ABSTRACT

An ultrasonic diagnosis apparatus according to an embodiment includes a controller, a processor, and an image generator. The controller selects at least one transducer element in a reception aperture formed of a transducer element group arranged in a predetermined direction, based on at least a deflection angle of an ultrasonic wave transmitted to a subject. The processor performs processing on at least one reception signal of a plurality of reception signals generated in the reception aperture such that a signal intensity of a reception signal generated in the at least one transducer element selected by the controller is reduced to be lower than a signal intensity of reception signals generated in transducer elements other than the at least one transducer element, to output the reception signal of the reception aperture. The image generator generates ultrasonic image data, based on the reception signal of the reception aperture.

21 Claims, 19 Drawing Sheets

(51) Int. Cl.
*A61B 8/00* (2006.01)
*G01S 15/89* (2006.01)
*G01S 7/52* (2006.01)

(52) U.S. Cl.
CPC .......... *A61B 8/5207* (2013.01); *A61B 8/5269* (2013.01); *A61B 8/54* (2013.01); *G01S 7/52046* (2013.01); *G01S 15/8927* (2013.01); *G01S 15/8995* (2013.01); *G01S 7/52038* (2013.01); *G01S 15/8979* (2013.01); *G01S 15/8993* (2013.01)

(58) Field of Classification Search
CPC ............. G01S 15/8979; G01S 15/8993; G01S 15/8995; G01S 15/8927; G01S 7/52046; G01S 7/52038
See application file for complete search history.

ULTRASONIC DIAGNOSIS APPARATUS AND IMAGE PROCESSING METHOD

CROSS-REFERENCE TO RELATED APPLICATIONS

This application is based upon and claims the benefit of priority from Japanese Patent Application No. 2014-023624, filed on Feb. 10, 2014, the entire contents of all of which are incorporated herein by reference.

FIELD

Embodiments described herein relate generally to an ultrasonic diagnosis apparatus and an image processing method.

BACKGROUND

Various methods are performed in conventional art to reduce multiple reflection of an ultrasonic image (B mode image) that obstructs diagnosis. An example of the methods is a known method using spatial compounding, in which a plurality of B mode images obtained by varying a deflection angle of ultrasound transmission and reception are compounded by arithmetic mean. In addition, an application of the method is a known method of estimating a degree and a position of a multiple reflection echo component from a plurality of B mode images having different deflection angles, and adaptively controlling a weight in arithmetic mean based on an estimation result.

However, the above method of compounding a plurality of images having different deflection angles cannot avoid influence of reduction in amplitude in the case of increasing the deflection angle, due to restriction of element factors.

DETAILED DESCRIPTION

An ultrasonic diagnosis apparatus according to an embodiment includes a controller, a processor, and an image generator. The controller selects at least one transducer element in a reception aperture formed of a transducer element group arranged in a predetermined direction, based on at least a deflection angle of an ultrasonic wave transmitted to a subject. The processor performs processing on at least one reception signal of a plurality of reception signals generated in the reception aperture such that a signal intensity of a reception signal generated in the at least one transducer element selected by the controller is reduced to be lower than a signal intensity of reception signals generated in transducer elements other than the at least one transducer element among transducer elements forming the reception aperture, to output the reception signal of the reception aperture. The image generator generates ultrasonic image data, based on the reception signal of the reception aperture that is output by the processor.

Embodiments of an ultrasonic diagnosis apparatus are described in detail below with reference to the drawings.

First Embodiment

Figure 1:
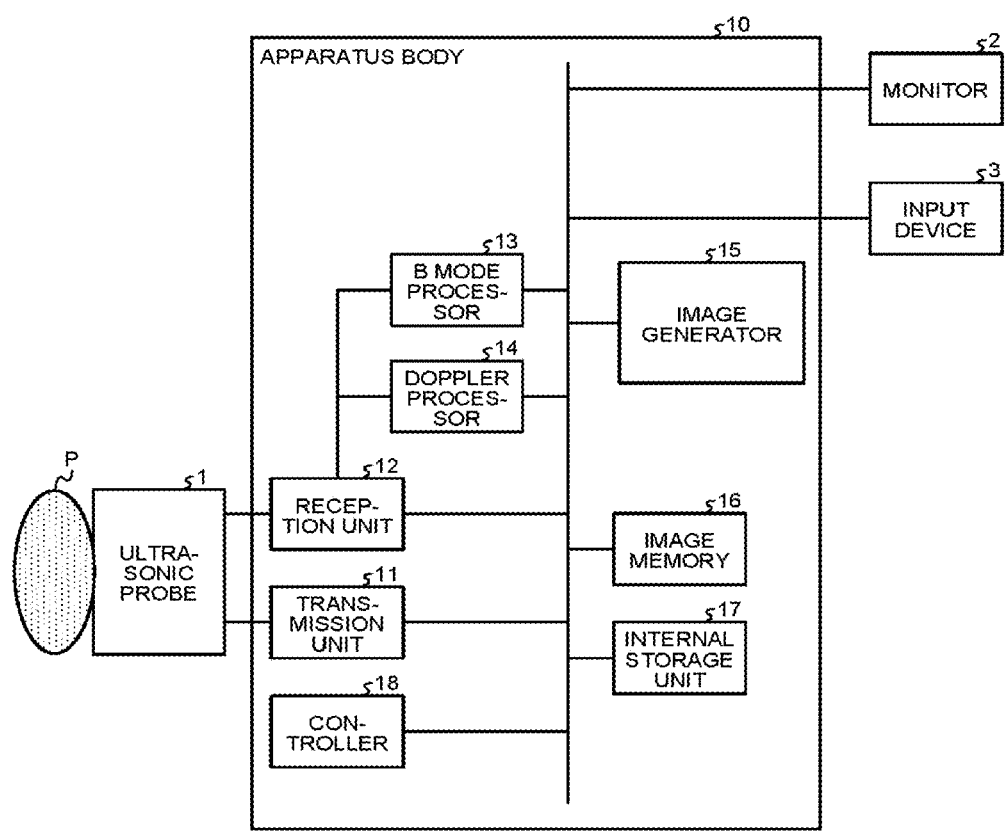
FIG. 1 is a diagram for explaining a configuration example of an ultrasonic diagnosis apparatus according to a first embodiment.

First, a configuration of the ultrasonic diagnosis apparatus according to a first embodiment is described. FIG. 1 is a block diagram illustrating a configuration example of the ultrasonic diagnosis apparatus according to the first embodiment. As illustrated in FIG. 1, the ultrasonic diagnosis apparatus according to the first embodiment includes an ultrasonic probe 1, a monitor 2, an input device 3, and an apparatus body 10.

The ultrasonic probe 1 includes a transducer element group formed of a plurality of transducer elements (for example, piezoelectric transducer elements) that are arranged in a predetermined direction. The transducer elements produce an ultrasonic wave based on a drive signal supplied from a transmission unit 11 of the apparatus body 10 described later. The transducer elements of the ultrasonic probe 1 receive a reflected wave from a subject P and convert the received reflected wave into an electrical signal. The ultrasonic probe 1 additionally includes a matching layer provided to the transducer elements and a backing material for preventing propagation of ultrasonic waves backward of the transducer elements.

When an ultrasonic wave is transmitted from the ultrasonic probe 1 to the subject P, the transmitted ultrasonic wave is successively reflected on an acoustic impedance discontinuous surface in living tissue of the subject P and received as reflected waves by the transducer elements of the ultrasonic probe 1. The reflected waves are converted into reflected-wave signals (reception signals) serving as electrical signals by the transducer elements that have received the reflected waves. The amplitude of the reflected-wave signal produced by each transducer element depends on the difference of acoustic impedance on the discontinuous surface on which the ultrasonic wave is reflected. In a case where the transmitted ultrasonic pulse is reflected at the moving blood flow or a surface such as the heart wall, the reflected-wave signal undergoes a frequency shift due to the Doppler effect, depending on the velocity component of the moving body relative to the ultrasound transmission direction.

The ultrasonic probe 1 is detachably connected with the apparatus body 10. The ultrasonic probe 1 connected to the apparatus body 10 is a one-dimensional (1D) array probe that includes a transducer element line in which transducer elements that are arranged in a predetermined direction are arranged in a line, and scans the subject P in a two-dimensional manner. As another example, the ultrasonic probe 1 connected to the apparatus body 10 is, for example, a mechanical four-dimensional (4D) probe that scans the subject P in a three-dimensional manner, by swinging a transducer element line at a predetermined angle (swinging angle). As another example, the ultrasonic probe 1 is, for example, a two-dimensional (2D) array probe in which a plurality of transducer elements are arranged in a two-dimensional manner, that is, a plurality of transducer element lines are arranged, to scan the subject P in a three-dimensional manner.

The following explanation illustrates the case where a one-dimensional array probe is used as the ultrasonic probe 1. Examples of the one-dimensional array probe are a linear type ultrasonic probe and a convex ultrasonic probe that move an aperture (a transmission aperture and a reception aperture) in the transducer element line to perform ultrasonic scan. Another example of the one-dimensional array probe is a sector type ultrasonic probe that deflects the scan direction with the positions of the aperture (a transmission aperture and a reception aperture) fixed in the transducer element line to perform ultrasonic scan. The predetermined direction in which the transducer elements are arranged differs according to the type of the ultrasonic probe 1. For example, the transducer elements are arranged in a straight line in the linear type ultrasonic probe. As another example, the transducer elements are arranged in an arc shape with a certain curvature in the convex type ultrasonic probe.

The input device 3 includes a mouse, a keyboard, a button, a panel switch, a touch command screen, a foot-switch, a trackball, and a joystick. The input device 3 accepts varieties of setting requests from the operator of the ultrasonic diagnosis apparatus and transfers the accepted setting requests to the apparatus body 10.

The monitor 2 displays a graphical user interface (GUI) for the operator of the ultrasonic diagnosis apparatus to input varieties of setting requests using the input device 3 and displays ultrasonic image data or other data generated in the apparatus body 10.

The apparatus body 10 is a device that generates ultrasonic image data based on the reflected-wave signal serving as a reception signal generated by each transducer element of the ultrasonic probe 1 and includes the transmission unit 11, a reception unit 12, a B mode processor 13, a Doppler processor 14, an image generator 15, an image memory 16, an internal storage unit 17, and a controller 18, as illustrated in FIG. 1.

The transmission unit 11 controls transmission directivity in ultrasound transmission, based on instructions of the controller 18 described later. Specifically, the transmission unit 11 is a transmission beam-former. More specifically, the transmission unit 11 includes a rate pulser generator, a transmission delay unit, and a transmission pulser to supply a drive signal to the ultrasonic probe 1. The rate pulser generator repeatedly generates, at a predetermined rate frequency (pulse repetition frequency (PRF)), rate pulses for forming ultrasonic waves to be transmitted. With the rate pulses passed through the transmission delay unit to have different transmission delays, voltage is applied to the transmission pulser. That is, the transmission delay unit provides necessary transmission delays for the respective transducer elements to individual rate pulses generated by the rate pulser generator, in order to concentrate ultrasonic waves generated from the ultrasonic probe 1 into a beam and determine the transmission directivity. The transmission pulser applies a drive signal (drive pulse) to the ultrasonic probe 1 at a timing based on such a rate pulse.

The drive pulse is transmitted from the transmission pulser through a cable to the transducer element in the ultrasonic probe 1 and thereafter converted from an electrical signal to mechanical vibration in the transducer elements. The mechanical vibration is transmitted as an ultrasonic wave in the inside of the living body. The ultrasonic waves having transmission delays different among transducer elements converge and propagate in a predetermined direction. The transmission delay unit adjusts the transmission direction from the transducer element surfaces as desired by changing the transmission delays provided to individual rate pulses. The transmission unit 11 provides transmission directivity by controlling the number and positions (transmission aperture) of transducer elements for use in transmission of ultrasonic beams and the transmission delays corresponding to the positions of the respective transducer elements that constitute the transmission aperture.

The transmission unit 11 has a function capable of instantaneously changing a transmission frequency, a transmission drive voltage, and the like for executing a predetermined scan sequence, based on an instruction from the controller 18 described later. In particular, the transmission drive voltage is changed by a linear-amplifier type oscillator circuit capable of instantaneously changing its value or a mechanism for electrically switching a plurality of power supply units.

The reflected wave of the ultrasonic wave transmitted by the ultrasonic probe 1 reaches the transducer elements in the ultrasonic probe 1 and is then converted from mechanical vibration into an electrical signal (reflected-wave signal) for input to the reception unit 12.

Figure 2:
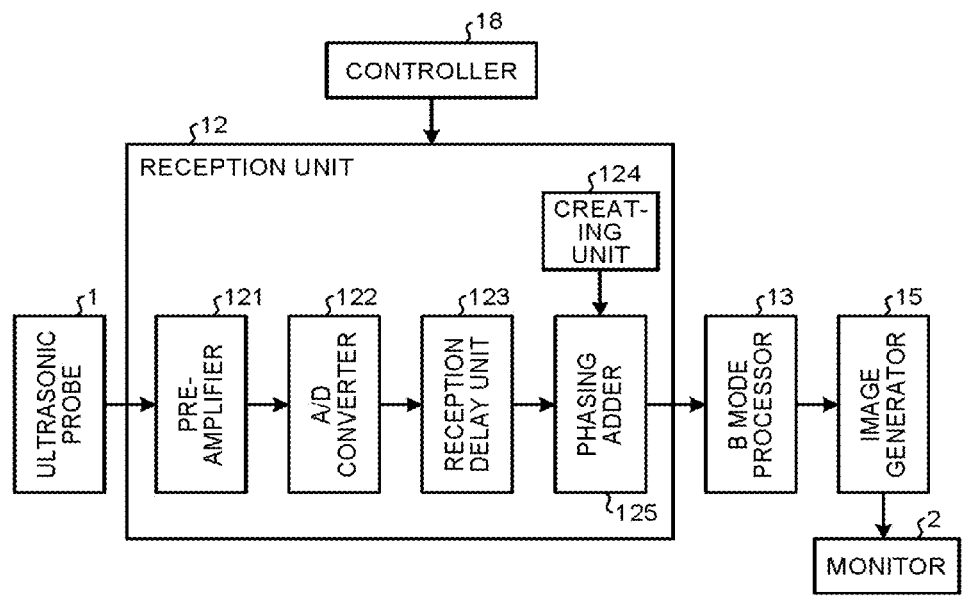
FIG. 2 is a diagram for explaining a configuration example of a reception unit according to the first embodiment.

The reception unit 12 controls reception directivity in ultrasound reception, based on an instruction of the controller 18 described later. Specifically, the reception unit 12 is a reception beam-former. FIG. 2 is a diagram for explaining a configuration example of the reception unit according to the first embodiment. For example, the reception unit 12 includes a pre-amplifier 121, an analog/digital (A/D) converter 122, a reception delay unit 123, a creating unit 124, and a phasing adder 125, as illustrated in FIG. 2, and performs varieties of processing on the reflected-wave signal generated by each transducer element of the ultrasonic probe 1 to generate reflected-wave data (reception signal) for each reception scan line. For example, the reflected-wave data is converted into ultrasonic image data (B mode image data) by a process performed by the B mode processor 13 and the image generator 15 described later, and output to the monitor 2, as illustrated in FIG. 2.

The pre-amplifier 121 performs gain adjustment by amplifying the reflected-wave signal for each channel. The A/D converter 122 converts the reflected-wave signal having the gain corrected from analog to digital, to convert the gain-corrected reflected-wave signal into digital data. The reception delay unit 123 provides the digital data with a reception delay (reception delay time) necessary to determine reception directivity. Specifically, the reception delay unit 123 provides an output signal of each transducer element with a reception delay, and thereby signals from the same sample point of the reception scan line being input to the phasing adder 125. As described above, the reception unit 12 provides reception directivity, by controlling the number and the positions (reception aperture) of the transducer elements used for reception of the reflected waves and the reception delays corresponding to the positions of the transducer elements forming the reception aperture. The reception delays differ according to the positions of the transducer elements and the positions of the reception focus.

The reception unit 12 is capable of executing dynamic variable aperture focus (DVAF). In the case of performing DVAF, the reception unit 12 reduces the reception aperture width to narrow a short-distance reception beam, when the reception unit 12 receives a signal returned from a close position. In the case of performing DVAF, the reception unit 12 increases the reception aperture width in accordance with the distance, when the reception unit 12 receives a signal returned from a distant position, because the larger reception aperture width provides a stronger focus. The reception aperture width is set by a preset "F-number". The value "F-number" is defined by a ratio of the depth of the reception focus to the reception aperture width, and can be changed as desired by the operator. In the case of performing DVAF, the reception unit 12 changes the reception aperture width in each depth position, in accordance with the "F-number". Specifically, the reception unit 12 sets the reception aperture with a reception aperture width determined based on the reception focus position and the "F-number" such that the reception scan line serves as the center thereof.

The phasing adder 125 performs addition (phasing addition) of the reflected-wave signals (digital data) provided with the reception delays by the reception delay unit 123. Specifically, the phasing adder 125 adds signals received by the respective transducer elements of the reception aperture from the same sample point. Addition performed by the phasing adder 125 emphasizes a reflected component from a direction according to the reception directivity for the reflected-wave signals. The signal that is output by the phasing adder 125 is output to the following processor as reflected-wave data (reception signal).

The reception unit 12 performs reception apodization. Specifically, the phasing adder 125 weights the signals received by the respective transducer elements of the reception aperture from the same sample point with an aperture function (apodization function), and thereafter performs phasing addition. The creating unit 124 illustrated in FIG. 2 creates the aperture function under the control of the controller 18 described later. The aperture function (reception aperture function) is a function with weights that are set for the respective positions of the transducer elements.

The phasing adder 125 weights the signals received by the respective transducer elements forming the reception aperture with an aperture function created by the creating unit 124, and thereafter subjects the signals to phasing addition. In the case of performing DVAF, the reception unit 12 corrects the reception sensitivity, together with adjustment of the reception aperture width. In the case of performing DVAF, the creating unit 124 creates an aperture function for each of reception apertures having different aperture widths according to the depth position. The aperture function created by the creating unit 124 in the first embodiment will be described in detail later.

Various forms may be selected as the form of the output signal from the phasing adder 125, such as the case where the output signal is a signal including phase information and called radio frequency (RF) signal or IQ signal, or amplitude information after envelope detection.

The B mode processor 13 generates data (B mode data) representing the signal intensity (amplitude intensity) for each sample point by brightness of luminance by performing logarithmic amplification, envelope detection, logarithmic compression, or other processing on the reflected-wave data serving as a reception signal that is generated and output by the reception unit 12.

The Doppler processor 14 performs frequency analysis on the reflected-wave data serving as a reception signal that is generated and output by the reception unit 12, to generate data (Doppler data) in which movement information of a moving body based on the Doppler effect is extracted in a scan area. Specifically, the Doppler processor 14 generates Doppler data in which the average velocity, the variance, the power value, or the like is extracted as the movement information of the moving body over many points. Here, the moving body is, for example, blood flow, tissue of the heart wall or other parts, or a contrast medium.

The ultrasonic diagnosis apparatus according to the present embodiment is capable of performing harmonic imaging such as contrast harmonic imaging (CHI) and tissue harmonic imaging (THI).

For example, in harmonic imaging, imaging methods are performed such as amplitude modulation (AM), phase modulation (PM), and AMPM being a combination of AM and PM. In AM, PM, and AMPM, ultrasound transmission is performed a plurality of times with different amplitudes and phases for the same scan line. In this manner, the reception unit 12 generates a plurality of reflected-wave data (reception signals) for each scan line. The reception unit 12 or the B mode processor 13 performs addition or subtraction according to the modulation method on the reflected-wave data (reception signals) of each scan line, to extract a harmonic component. The B mode processor 13 performs envelope detection on the reflected-wave data (reception signal) of the harmonic component, to generate B mode data.

For example, in the case of performing PM, the transmission unit 11 transmits ultrasonic waves with the same amplitude and inverted phase polarities, such as (−1, 1), twice in each scan line, by a scan sequence set by the controller 18. The reception unit 12 generates a reception signal obtained by transmission of "−1" and a reception signal obtained by transmission of "1". The reception unit 12 or the B mode processor 13 adds the two reception signals. The addition generates a signal in which a basic wave component is removed and a second harmonic component mainly remains. The B mode processor 13 performs envelope detection and the like on the signal, to generate B mode data for THI or B mode data for CHI.

THI includes a method that has put to practical use in which imaging is performed using a second harmonic component and a difference tone component that are included in a reception signal. In imaging using a difference tone component, for example, the ultrasonic probe 1 transmits a transmission ultrasonic wave having a composite waveform obtained by combining a first basic wave having a center frequency of "f1" with a second basic wave having a center frequency of "f2" that is greater than "f1". The composite waveform is obtained by combining the waveform of the first basic wave with the waveform of the second basic wave with their phases adjusted to generate a difference tone component having the same polarity as that of the second harmonic component. The transmission unit 11 transmits a transmission ultrasonic wave having the composite waveform, for example, twice with inverted phases. In such a case, the reception unit 12 generates two reception signals corresponding to the respective transmissions. Thereafter, the reception unit 12 or the B mode processor 13 adds the two reception signals. The addition generates a signal in which a basic wave component is removed and a second harmonic component mainly remains. The B mode processor 13 performs envelope detection and the like on the signal, to generate B mode data for THI.

The image generator 15 generates ultrasonic image data from the data generated by the B mode processor 13 and the Doppler processor 14. Specifically, the image generator 15 generates B mode image data representing the intensity of the reflected wave by brightness, from the B mode data generated by the B mode processor 13. The image generator 15 also generates color Doppler image data representing moving-body information from the Doppler data generated by the Doppler processor 14. The color Doppler image data serves as an average velocity image, a variance image, a power image, or an image formed of a combination thereof.

Here, the image generator 15, in general, generates display-purpose ultrasonic image data by scan-converting a scan line signal sequence of ultrasonic scan into a scan line signal sequence in a video format typically of televisions. Specifically, the image generator 15 generates display-purpose ultrasonic image data by performing coordinate transformation in accordance with the mode of ultrasonic scan with the ultrasonic probe 1. The image generator 15 also combines character information of various parameters, scales, and body marks with ultrasonic image data.

That is, B mode data and Doppler data are ultrasonic image data before the scan conversion processing, and the data generated by the image generator 15 is display-purpose ultrasonic image data after the scan conversion processing. B mode data and Doppler data are also referred to as raw data.

When a mechanical four-dimensional probe or a two-dimensional array probe used as the ultrasonic probe 1, the transmission unit 11, the reception unit 12, the B mode processor 13, the Doppler processor 14, and the image generator 15 can perform processing to generate three-dimensional ultrasonic image data (volume data). For example, when the subject P is scanned in a three-dimensional manner, the transmission unit 11 transmits a three-dimensional ultrasonic beam from the ultrasonic probe 1. The reception unit 12 generates three-dimensional reflected-wave data from a three-dimensional reflected-wave signal received by the ultrasonic probe 1.

Next, the B mode processor 13 generates three-dimensional B mode data from the three-dimensional reflected-wave data. The Doppler processor 14 generates three-dimensional Doppler data from the three-dimensional reflected-wave data. The image generator 15 performs coordinate transformation on the three-dimensional B mode data generated by the B mode processor 13, to generate three-dimensional B mode image data. The image generator 15 performs coordinate transformation on the three-dimensional Doppler data generated by the Doppler processor 14, to generate three-dimensional Doppler image data.

In addition, the image generator 15 performs rendering on the volume data, to generate varieties of two-dimensional image data for displaying the volume data on the monitor 2. An example of the rendering performed by the image generator 15 is a process of generating MPR image data from volume data by multi planar reconstruction (MPR). Another example of the rendering performed by the image generator 15 is volume rendering (VR) that generates two-dimensional image data reflecting three-dimensional information.

The image memory 16 is a memory for storing therein display image data generated by the image generator 15. The image memory 16 may also store therein data generated by the B mode processor 13 and the Doppler processor 14. The B mode data and the Doppler data stored in the image memory 16 can be invoked by the operator, for example, after diagnosis, and is turned into display-purpose ultrasonic image data through the image generator 15.

The internal storage unit 17 stores therein control programs for ultrasound transmission and reception, image processing, and display processing, and varieties of data such as diagnosis information (for example, patient ID and doctor's opinion), diagnosis protocols, and varieties of body marks. For example, the internal storage unit 17 stores therein a scan sequence for performing harmonic imaging. The internal storage unit 17 is also used for retaining data stored by the image memory 16, as necessary.

The controller 18 controls the entire processing in the ultrasonic diagnosis apparatus. Specifically, the controller 18 controls the processes in the transmission unit 11, the reception unit 12, the B mode processor 13, the Doppler processor 14, and the image generator 15, based on various setting requests input from the operator through the input device 3, and various control programs and various data read from the internal storage unit 17. The controller 18 performs control such that the display-purpose ultrasonic image data stored in the image memory 16 displays on the monitor 2. The controller 18 according to the first embodiment controls reception apodization as control of ultrasound transmission and reception. The control will be described later.

With the entire configuration of the ultrasonic diagnosis apparatus explained above according to the first embodiment, the ultrasonic diagnosis apparatus according to the first embodiment generates and displays B mode image data.

Various methods are performed in conventional art to reduce multiple reflection of an ultrasonic image (B mode image) that obstructs diagnosis. An example of the methods is a known method using spatial compounding in which a plurality of B mode images with different deflection angles of ultrasound transmission and reception are compounded by arithmetic mean. In addition, an application of the method is a known method of estimating a degree and a position of a multiple reflection echo component from a plurality of B mode images having different deflection angles, and adaptively controlling a weight in arithmetic mean based on an estimation result. However, the above method of compounding a plurality of images having different deflection angles cannot avoid influence of reduction in amplitude in the case of increasing the deflection angle, due to restriction of element factors.

Another method for reducing multiple reflection has been proposed. The method is a method of creating reception apodization including a multiple reflection component as less as possible. Such a method uses, for example, reception apodization with an aperture function that weights the central part of the reception aperture with "0". Hereinafter, the method of weighting the central part of the reception aperture with "0" is referred to as "premise method". However, the premise method leaves the case where a multiple reflection component cannot be reduced. In the present embodiment, a method is explained for solving the problem of the premise method.

Figure 3:
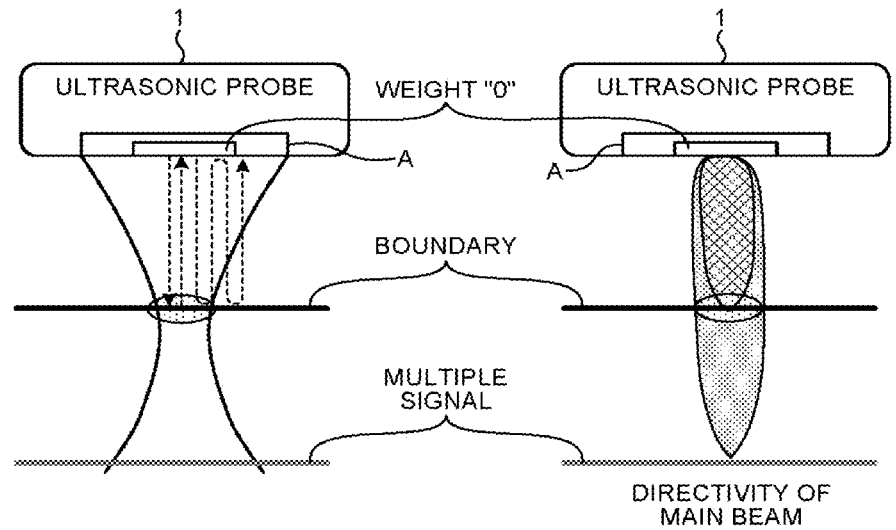
FIG. 3 is a diagram (1) for explaining a premise method.
Figure 4:
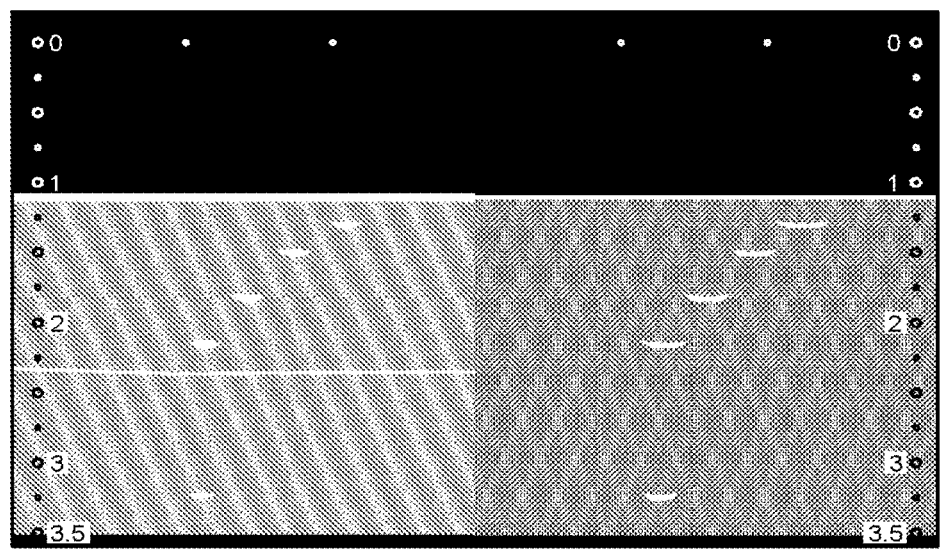
FIG. 4 is a diagram (2) for explaining the premise method.

The following is explanation of the above premise method and the problem of the premise method with reference to FIG. 3 to FIG. 8, and explanation of reception apodization performed by the ultrasonic diagnosis apparatus according to the present embodiment. FIG. 3 and FIG. 4 are diagrams for explaining the premise method, and FIG. 5 to FIG. 8 are diagrams for explaining the problem of the premise method.

The element "A" illustrated in FIG. 3 is a reception aperture that is set in a certain reception scan line in the ultrasonic probe 1. FIG. 3 also illustrates the shape of an ultrasonic beam transmitted from a transmission aperture having the same width as that of the reception aperture A. FIG. 3 also illustrates, with a line segment, a "boundary" at which a large difference in acoustic impedance occurs in the scan cross section due to a structure in the subject P that causes multiple reflection. In the example illustrated in FIG. 3, the focus of the transmission ultrasonic beam generally corresponds to the depth of the "boundary".

The left drawing of FIG. 3 illustrates, with broken lines, an aspect of one-time multiplexing caused by the "boundary" formed of the above structure. In the example illustrated in FIG. 3, the reflected wave obtained by reflecting the transmission ultrasonic wave by the boundary reaches the surface (probe surface) of the ultrasonic probe 1. After the reflected wave is reflected by the probe surface, the reflected wave is reflected by the "boundary" again, and reaches the surface of the ultrasonic probe 1. A signal (multiple reflection signal) received by the reception aperture A by one-time multiplexing caused as described above is displayed as if the signal were a signal from a boundary located in a position deeper than that of the "boundary". FIG. 3 illustrates a line segment displayed as a multiple reflection signal as "multiple signal".

In addition, the right drawing of FIG. 3 schematically illustrates a main seam of a true reflection signal that is reflected by the "boundary" formed of the structure and received by the reception aperture A, and a main beam of a multiple reflection signal that is received by the reception aperture A as if the multiple reflection signal were reflected at the position of the "multiple signal". As illustrated in the right drawing of FIG. 3, the directivity of the main beam of the reflection signal has the same direction as that of the main beam of the multiple reflection signal. Specifically, the directivities of the two main beams have a direction perpendicular to the reception aperture A toward the center of the reception aperture A, as illustrated in the right drawing of FIG. 3.

By reception delay processing performed with the reception focus set to a position around the structure, the wave surface of the reflection signal derived from the structure has a uniform phase in all the transducer elements forming the reception aperture A. By contrast, even when reception delay processing is performed with reception focus set to the position of the structure, the wave surface of the multiple reflection signal has a uniform phase only in the transducer elements of a limited range in the central part of the reception aperture A.

Specifically, a signal in which a true signal derived from the structure is mainly extracted can be obtained by performing phasing addition on reflected-wave signals serving as reception signals generated in the transducer elements other than the transducer elements located in the central part of the reception aperture A, after the reception delay processing is performed. Thus, in the premise method, for example, reception apodization is performed as illustrated in FIG. 3, using an aperture function with a weight of "0" for the range having a predetermined width and having a central position (position of the center of gravity) of the reception aperture A as the center, and with a weight of "1" outside the range. For example, the predetermined width is a width half the reception aperture width.

FIG. 4 illustrates a screen in which B mode image data of a phantom obtained by ordinary reception apodization is disposed on the left side, and B mode image data of a phantom obtained by reception apodization of the above premise method is disposed on the right side. In ordinary reception apodization, for example, an aperture function is set in which a weight for the central part of the reception aperture A is greater than a weight for the parts other than the central part of the reception aperture A. For example, ordinary reception apodization uses an aperture function that provides a weight with a "hamming window". The phantom used for imaging in FIG. 4 is a phantom in which a strong reflector that forms a boundary is disposed around a depth of 120 mm, and a plurality of wires are arranged in positions deeper than the strong reflector. In the B mode image data on the left side of FIG. 4, a multiple artifact due to the strong reflector is generated around a depth of 240 mm. By contrast, a multiple artifact due to the strong reflector is almost removed in the B-mode image data on the right side of FIG. 4. Specifically, FIG. 4 demonstrates that the premise method can remove a multiple signal superimposed on B mode image data imaged by a conventional method, with a weight of exactly or almost 0 for the central part of the reception aperture A.

However, the above premise method is effective for the case illustrated in FIG. 3. Specifically, the example illustrated in FIG. 3 is an example in which "the boundary of the structure in the subject P is parallel with the probe surface" and "the direction of ultrasound transmission and reception is perpendicular to the probe surface". Consequently, "the directivity of the main beam of the reflection signal has the same direction as the directivity of the main beam of the multiple reflection signal", and "the reception position of the multiple reflection signal is located in substantially the central part of the reception aperture like the reception position of the reflection signal". When the above conditions are satisfied, the above premise method enables removal of a multiple signal with a weight of "0" that is set for the central part of the aperture.

Figure 5:
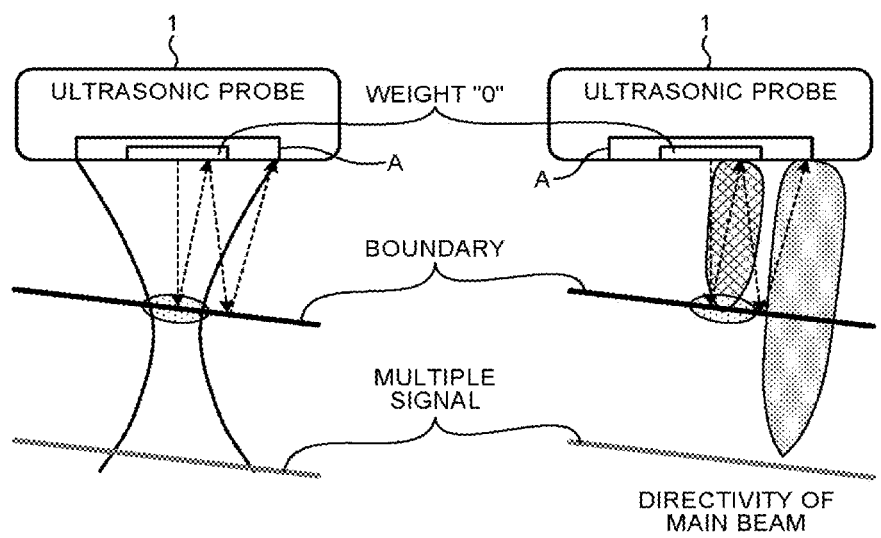
FIG. 5 is a diagram (1) for explaining a problem of the premise method.
Figure 6:
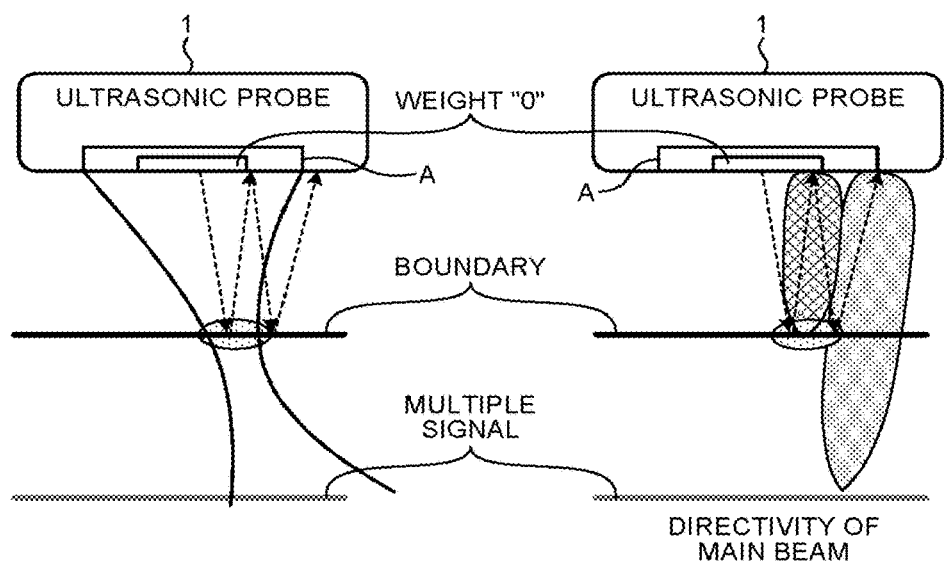
FIG. 6 is a diagram (2) for explaining the problem of the premise method.

However, the above premise method may not be effective when the boundary of the structure is inclined with respect to the probe surface, as illustrated in FIG. 5. FIG. 5 illustrates one-time multiple reflection that occurs when the boundary of the structure is inclined with respect to the probe surface, although the direction of the transmission beam is perpendicular to the probe surface. In addition, the above premise method may not be effective in the case where the transmission beam is steered as illustrated in FIG. 6. FIG. 6 illustrates one-time multiple reflection that occurs when the direction of the transmission beam is inclined with respect to the probe surface, although the probe surface is parallel with the boundary of the structure.

As illustrated in the left drawing of FIG. 5 and the left drawing of FIG. 6, the reflection signal reflected by the boundary of the structure is made incident on the probe surface obliquely. For this reason, when multiple reflection occurs, the multiple reflection signal is received by a transducer element in a position located closer to the end than the position of the transducer element that has received the reflection signal of the structure is, due to inclination (inclination of the boundary of the structure or inclination of the transmission beam). Specifically, as illustrated in the right drawing of FIG. 5 and the right drawing of FIG. 6, the directivity of the main beam of the reflection signal from the structure does not match up with the directivity of the main beam of the multiple signal, due to inclination of the boundary of the structure or inclination of the transmission beam.

As described above, the phenomena illustrated in FIG. 5 and FIG. 6 occur, when the directivity of the main beam of the reflection signal is different from the directivity of the main beam of the multiple signal. In the examples illustrated in FIG. 5 and FIG. 6, the reflection signal from the structure is received at a position of the transducer element with a weight of "0". However, in the examples illustrated in FIG. 5 and FIG. 6, the multiple reflection signal is received at a position of the transducer element with a weight, due to relative relation between the direction of the transmission beam and the direction indicating the boundary of the structure. Consequently, when the premise method is applied to the cases illustrated in FIG. 5 and FIG. 6 to set the weight to exactly or almost "0" in the range including the central position of the reception aperture A, the reflection signal from the structure is reduced with the weight "0", and consequently imaging is performed in a state where the multiple reflection signal is not reduced at all.

Figure 7:
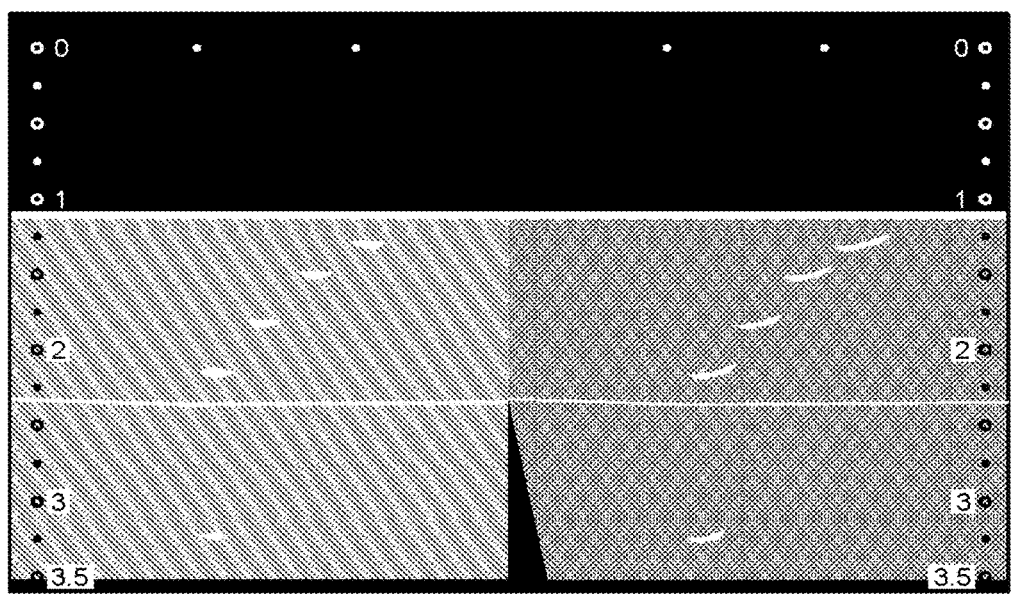
FIG. 7 is a diagram (3) for explaining the problem of the premise method.

The left image of FIG. 7 illustrates B mode image data of a phantom obtained by ordinary reception apodization, in the same manner as the left image of FIG. 4. The right image in FIG. 7 illustrates B mode image data of the same phantom obtained by reception apodization with a weight of "0" for the central part of the reception aperture, under the condition that "the direction of the transmission beam is inclined with respect to the probe surface, although the probe surface is parallel with the boundary of the structure" as illustrated in FIG. 6.

Comparison between the left and the right images of FIG. 7 has revealed that artifacts caused by a multiple reflection signal are generated in substantially the same manner in both the images, and that image deterioration still occurs even when the premise method is applied.

In addition, the above premise method may reduce azimuth resolution. For example, when compared the left and the right images of FIG. 4, the azimuth resolution for the wires is reduced in the right image to which the premise method is applied, in comparison with the left image without the premise method. Specifically, when the premise method is applied, the wires are depicted in a state of spreading in an azimuth direction in the right B mode image data of FIG. 4. Such reduction in azimuth resolution also occurs in the right B mode image data of FIG. 7 illustrating an example on which the premise method does not effectively act.

Figure 8:
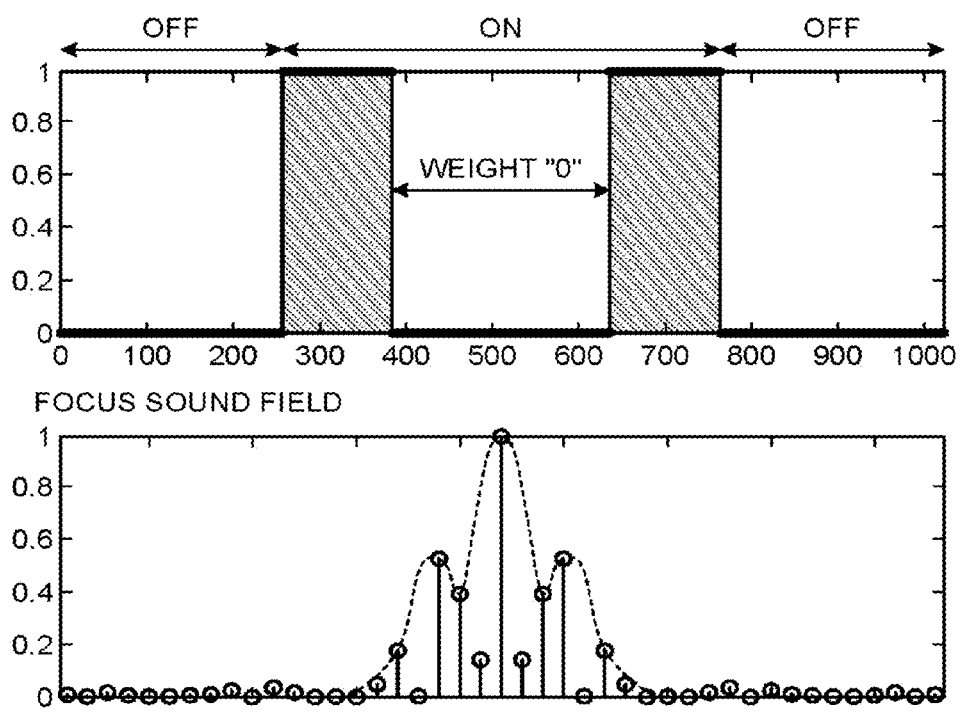
FIG. 8 is a diagram (4) for explaining the problem of the premise method.

The primary cause of the problem will be explained with reference to FIG. 8. The upper drawing of FIG. 8 illustrates the positions of the transducer elements of the ultrasonic probe 1 in the horizontal axis, and the weights of the aperture function in the vertical axis. The upper drawing of FIG. 8 also illustrates a range set as the reception aperture with "ON", and ranges that are not set as the reception aperture with "OFF". The upper drawing of FIG. 8 illustrates an aperture function with a weight "0" that is set for the central part of the reception aperture, and a weight "1" that is set for the parts of the reception aperture outside the range of the central part, as described above.

It is known that a sound field (amplitude distribution) around the focus is provided by Fourier transform of the aperture function. The lower drawing of FIG. 8 illustrates the focus sound field obtained by performing Fourier transform on the aperture function illustrated in the upper drawing of FIG. 8. Specifically, the lower drawing of FIG. 8 illustrates a sound field distribution at the focus. More specifically, the lower drawing of FIG. 8 illustrates a sound field distribution in an azimuth direction at the focus.

The lower drawing of FIG. 8 demonstrates that the "main-lobe/side-lobe ratio" increases in the sound field distribution around the focus by virtue of use of the aperture function with a weight of "0" for the central part of the reception aperture. Specifically, the lower drawing of FIG. 8 demonstrates that the side lobe relatively increases with respect to the main lobe, in the case of using an aperture function with a weight of "C" for the central part of the reception aperture. As a result, as illustrated in FIG. 4 and FIG. 7, azimuth resolution decreases in B mode image data obtained by imaging using the premise method. The above various problems also occur in the same manner in B mode image data obtained by THI.

To reduce multiple reflection, the ultrasonic diagnosis apparatus according to the first embodiment performs the following process. First, the controller 18 illustrated in FIG. 1 selects at least one transducer element in a reception aperture formed of at least one transducer element in a reception aperture formed of a transducer element group arranged in a predetermined direction, based on at least one of the following three parameters. The first parameter is a deflection angle of the ultrasonic wave transmitted to the subject P. The second parameter is an angle made between the predetermined direction and a direction indicating the boundary of the structure in the subject P. The third parameter is an angle made between a direction perpendicular to a normal direction where the predetermined direction intersects with a center of the transducer element group and the direction indicating the boundary. The second parameter is a parameter applied to the case where the ultrasonic probe 1 is a linear type ultrasonic probe. By contrast, the third parameter is a parameter applied to the case where the ultrasonic probe 1 is a convex type ultrasonic probe. These parameters will be described in detail later.

For example, the controller 18 calculates a reception position at which a multiple reflection component is received in the reception aperture, to select at least one transducer element in the reception aperture based on at least one of the above three parameters. As an example, the controller 18 calculates a reception position at which the main beam of multiple reflection is received in the reception aperture. Specifically, the controller 18 calculates the above reception position, based on the direction of ultrasound transmission and reception (direction of the transmission and reception beam) and the direction of the structure that causes multiple reflection. More specifically, the controller 18 calculates a reception position at which a multiple reflection component (such as the main beam of multiple reflection) is received in the reception aperture, based on the assumption that multiple reflection due to an angle made between the direction of the transmission and reception beam and the direction of the structure is mirror reflection. Then, the controller 18 selects at least one transducer element corresponding to the calculated reception position. For example, when the ultrasonic probe 1 is a linear type ultrasonic probe, the controller 18 selects at least one transducer element based on the first parameter and the second parameter. For example, when the ultrasonic probe 1 is a convex type ultrasonic probe, the controller 18 selects at least one transducer element based on the first parameter and the third parameter.

Under the control of the controller 18, the reception unit 12 functions as a processor that performs a process explained in the following. The reception unit 12 performs processing on at least one reception signal of a plurality of reception signals generated in the reception aperture such that a signal intensity of a reception signal generated in "the at least one transducer element in the reception aperture" selected by the controller 18 is reduced to be lower than a signal intensity of reception signals generated in transducer elements other than "the at least one transducer element" among transducer elements forming the reception aperture. Thereafter, the reception unit 12 outputs the reception signal of the reception aperture. The processing performed by the reception unit 12 may be referred to as "reduction processing" hereinafter.

For example, the controller 18 sets a range including the selected at least one transducer element as a reduction range. The reduction range is a range based on the reception position calculated by the controller 18. For example, the reduction range is a range including the reception position calculated by the controller 18 as the center of gravity. The reception unit 12 performs reduction processing such that information of the signal received in the reduction range is reduced to be lower than information of the signal received by ranges outside the reduction range in the reception aperture, and outputs the reception signal of the reception aperture. In the following explanation, the "reduction range" may be referred to as "range", "in the reduction range" may be referred to as "in the range", and "outside the reduction range" may be referred to as "outside the range". The image generator 15 generates ultrasonic image data based on the above reception signal of the reception aperture.

Specifically, under the control of the controller 18, the creating unit 124 illustrated in FIG. 2 creates an aperture function in which a weight in the range including at least one transducer element selected by the controller 18 is reduced to be lower than a weight outside the range. More specifically, the creating unit 124 creates an aperture function by setting a weight in the range (in the reduction range) to exactly or almost zero. The aperture function created by the creating unit 124 is set in the phasing adder 125.

The phasing adder 125 outputs a signal obtained by weighting the reception signals (reflected-wave signals) generated by the respective transducer elements forming the reception aperture with the aperture function and thereafter subjecting the weighted reception signals to phasing addition, as a reception signal of the reception aperture.

Specifically, the phasing adder 125 weights the signals that have been generated by the respective transducer elements forming the reception aperture and subjected to reception delay processing, with the aperture function, and adds the weighted signals, to obtain a reception signal of the reception aperture. The phasing adder 125 performs such processing for each reception scan line, and successively outputs reflected-wave data in the scan range to the B mode processor 13. With the reflected-wave data, the B mode processor 13 generates B mode data in the scan range, and the image generator 15 generates B mode image data from the B mode data in the scan range obtained from the B mode processor 13. The above processing is applicable to varieties of B mode imaging by THI, as well as ordinary B mode imaging. The above processing is also applicable to all two-dimensional scans performed with a linear type ultrasonic probe, a convex type ultrasonic probe, and a sector type ultrasonic probe, as a one-dimensional array probe. The above processing is also applicable to the case of performing three-dimensional scan using a mechanical four-dimensional probe or a two-dimensional array probe.

Specifically, in the first embodiment, reception apodization is performed to set an aperture function such that the position in which the weight is reduced (for example, the position where the weight is reduced to exactly or almost "0") in the reception aperture is always moved to a position where a multiple reflection signal is received. The position where a reflection signal or a multiple reflection signal is received in the reception aperture can be calculated based on the assumption that mirror reflection causes multiple reflection with an angle made between the direction of ultrasonic transmission and reception and the direction indicating the boundary of the structure.

Figure 9:
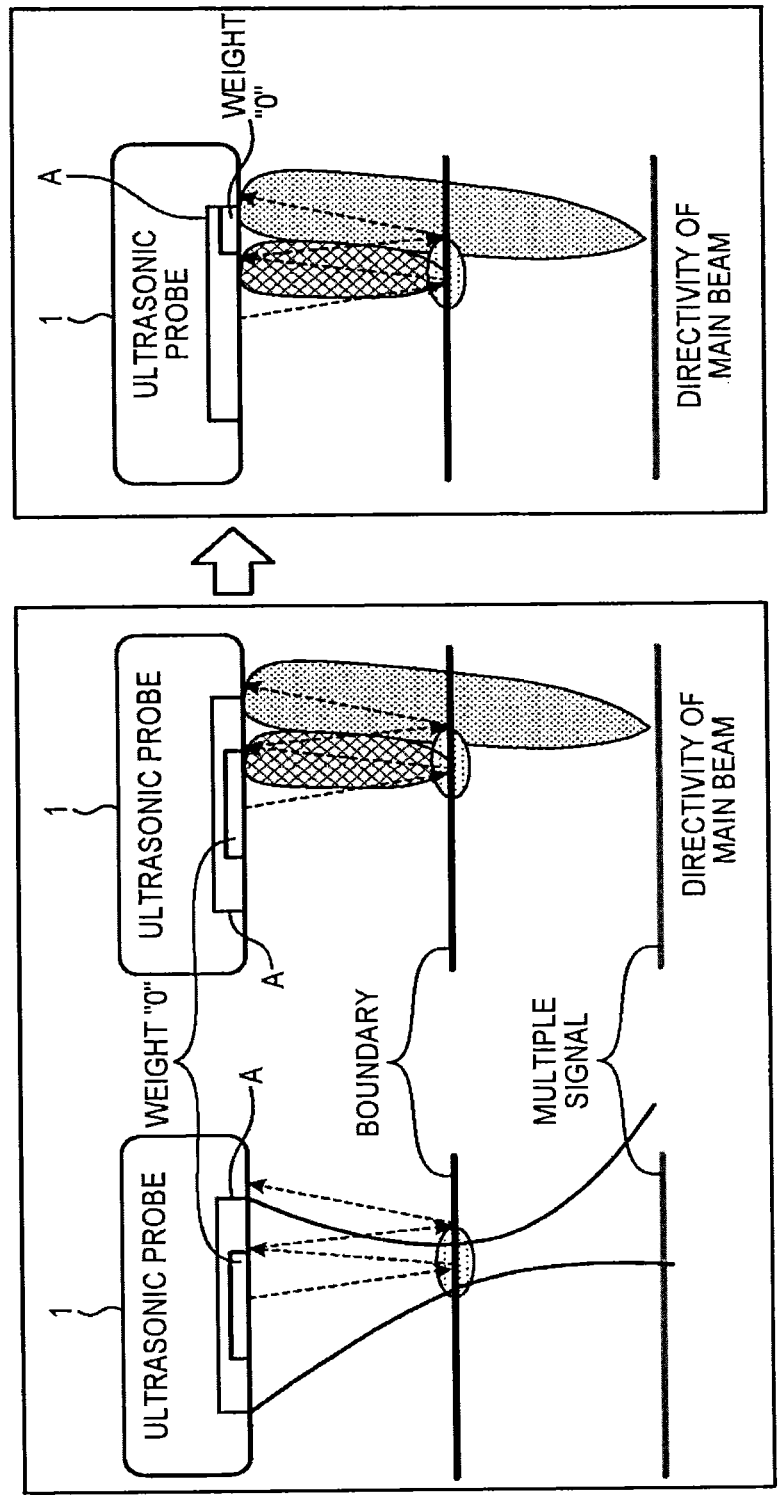
FIG. 9 is a diagram illustrating an outline of a first embodiment.

Accordingly, in the first embodiment, the position where a multiple reflection component (such as a main beam of multiple reflection) is received is calculated based on mirror reflection occurred by the direction of ultrasonic transmission and reception and the direction indicating the boundary of the structure, and an aperture function is set with a reduced weight in a predetermined range including the calculated position as a basis (such as the center of gravity). FIG. 9 is a diagram illustrating an outline of the first embodiment.

The left drawing of FIG. 9 is the same as FIG. 6, illustrating an example in which the boundary formed of the structure is horizontal and the transmission and reception beam is inclined. The controller 18 according to the first embodiment calculates the reception position (position of the transducer element) where the main beam of multiple reflection is received in the reception aperture A, based on the direction indicating the boundary of the structure and the direction of the transmission and reception beam. Thereafter, the controller 18 according to the first embodiment causes the creating unit 124 to create an aperture function in which the position of the center of gravity of the range with a weight "0" is shifted from the "central position of the reception aperture A" to the "calculated reception position". As a result, the present embodiment enables acquisition of a reception signal in which a multiple reflection component is substantially reduced and a true reflection component remains.

Reception apodization performed in the first embodiment may be referred to as "shift type reception apodization", and reception apodization performed by the above premise method may be referred to as "fixed type reception apodization" hereinafter.

Shift type reception apodization is performed by obtaining, by the controller 18, parameters explained with reference to FIG. 10A, FIG. 10B, FIG. 10C, and FIG. 10D. FIG. 10A, FIG. 10B, FIG. 10C, and FIG. 10D are diagrams for explaining parameters used in the first embodiment.

Figure 10A:
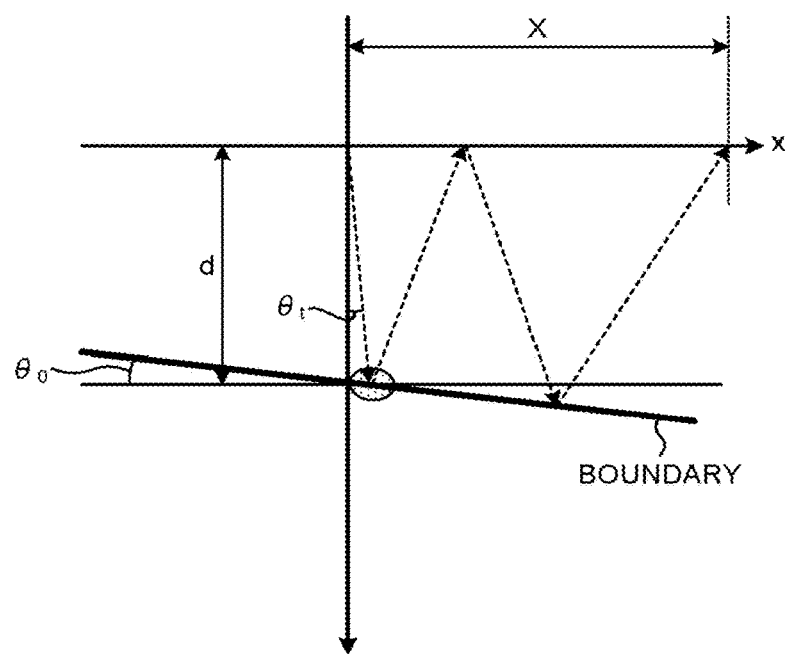
FIG. 10A is a diagram (1) for explaining parameters used in the first embodiment.
Figure 10B:
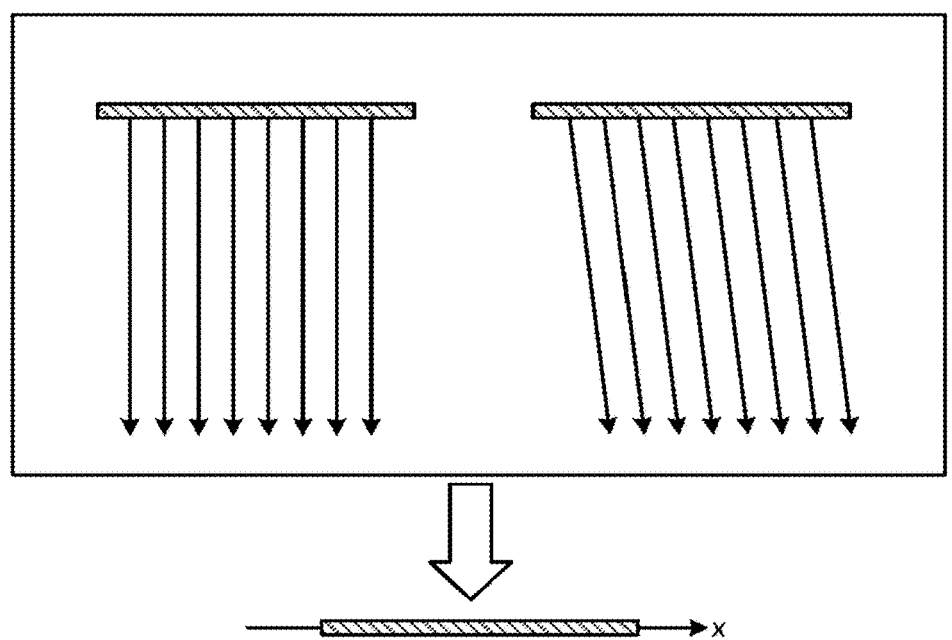
FIG. 10B is a diagram (2) for explaining the parameters used in the first embodiment.
Figure 10C:
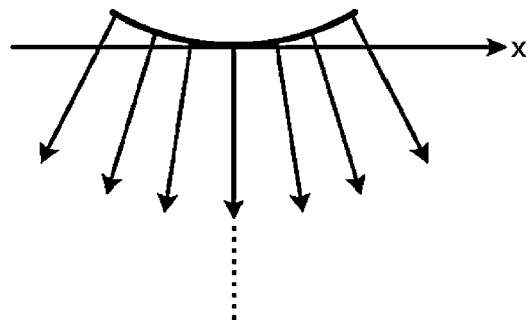
FIG. 10C is a diagram (3) for explaining the parameters used in the first embodiment.

FIG. 10A illustrates an axis defined from the predetermined direction in which the transducer elements are arranged with an x axis. A linear type ultrasonic probe in which the transducer elements are arranged in a straight line performs linear scan in which ultrasonic beams that are parallel between the transmission apertures are transmitted while the transmission aperture is moved, as illustrated in the upper drawing of FIG. 10B. In the case of using a linear type ultrasonic probe, the direction of the x axis is "the predetermined direction in which the transducer element group are arranged", as illustrated in the lower drawing of FIG. 10B. By contrast, a convex type ultrasonic probe in which the transducer elements are arranged in an arc shape performs offset sector scan in which ultrasonic beams are transmitted in a fan shape while the transmission aperture is moved, as illustrated in FIG. 10C. In the case of using a convex type ultrasonic probe, the direction of the x axis is a direction perpendicular to a normal direction where the predetermined direction intersects with the center of the transducer element group, as illustrated in the lower drawing of FIG. 10C.

In FIG. 10A, a downward arrow indicates a direction of a y axis (that is, the depth direction) that is orthogonal to the x axis and extends through the central position of the reception aperture. The direction of the y axis serves as the above normal direction in a convex type ultrasonic probe. In the following explanation, the central position of the reception aperture (and the transmission aperture) is explained as the origin (0, 0).

FIG. 10A also illustrates that an angle "$\theta_t$" between the transmission direction of the ultrasonic beam and the direction of the y axis is used as an example of the above first parameter "deflection angle of the ultrasonic wave". In the linear type ultrasonic probe, because ultrasonic beams transmitted from the respective transmission apertures are deflected with the same angle as illustrated in the right drawing of FIG. 10B, the "deflection angle of the ultrasonic wave" is easily defined as an angle made between the transmission direction of the ultrasonic beam and the direction of the y axis.

Figure 10D:
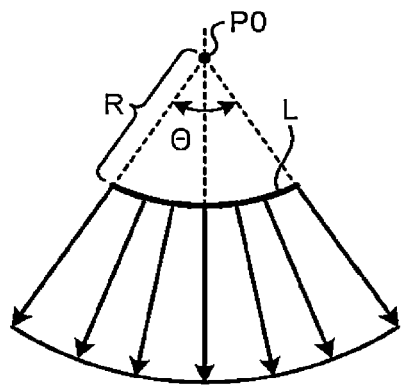
FIG. 10D is a diagram (4) for explaining the parameters used in the first embodiment.
Figure 10D:
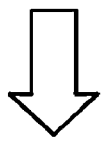
Figure 10D:
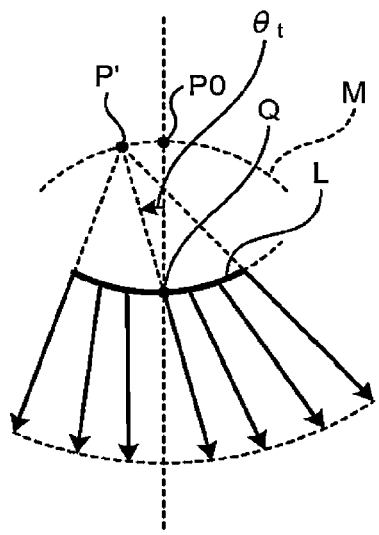

By contrast, in a convex type ultrasonic probe, the transmission direction of the ultrasonic beam is different for each transmission aperture as illustrated in FIG. 10C even when the ultrasonic beam is not deflected, and definition of the deflection angle thereof is different from that of a linear ultrasonic probe. The following is explanation of deflection of ultrasonic waves performed in a convex type ultrasonic probe. The upper drawing of FIG. 10D illustrates a convex type ultrasonic probe in which transducer elements are arranged along an arc L having a base point P0 as the center and having a curvature radius R. The convex type ultrasonic probe illustrated in the upper drawing of FIG. 10D transmits ultrasonic beams that spread in a fan shape with the base point P0 serving as the center, at an angle of view Θ. When the unit of Θ is radian, the length of the arc L is R×Θ.

When transmitted steering beams from the convex type ultrasonic probe, the base point P0 is moved along a circle M having a central position Q of the arc L as the center and a line segment PQ as the radius, as illustrated in the lower drawing of FIG. 10D. In the lower drawing of FIG. 10D, P' of a position where denotes a point obtained by moving the base point P0 by the deflection angle "$\theta_t$" along the circle M. The convex type ultrasonic probe transmits steering beams in an arc shape with the point P' serving as the center, as illustrated in the lower drawing of FIG. 10D. The deflection angle of the ultrasonic waves is defined as described above in a convex type ultrasonic probe.

In FIG. 10A, "$\theta_0$" denotes an angle made between the direction of the x axis and the direction indicating the boundary of the structure. The angle "$\theta_0$" is an example of the parameter that indicates the direction indicating the boundary of the structure, and an angle corresponding to the above "second parameter or the third parameter". The symbol "d" in FIG. 10A denotes a depth of a position where the ultrasonic beam transmitted at the angle "$\theta_1$" is first reflected in the boundary formed of the structure inclined with the angle "$\theta_0$". Specifically, "d" in FIG. 10A denotes a depth at which the structure is located on the scan line.

The symbol "X" in FIG. 10A denotes a distance from the central position of the reception aperture to, for example, the reception position where the main beam of multiple reflection is received in the reception aperture. Specifically, "X" is a reception position serving as a basis used for setting the reduction range and, for example, a position of the center of gravity (central position) of the range occupied by the transducer elements with a weight of exactly or almost "0" in the aperture function. The controller 18 calculates "X" by, for example, multiplying "d" by a function F ($\theta_t$, $\theta_0$) formulated with the angle "$\theta_t$" and the angle "$\theta_0$", to select "at least one transducer element" located in "X". The function F ($\theta_t$, $\theta_0$) will be explained in detail later using mathematical expressions.

The following is explanation of an example of shift type reception apodization performed under the control of the controller 18 according to the first embodiment, with reference to FIG. 11 to FIG. 16 and mathematical expressions. FIG. 11 to FIG. 16 are diagrams for explaining a process performed by the controller according to the first embodiment.

First, a method for obtaining varieties of parameters illustrated in FIG. 10A is explained hereinafter. The controller 18 is capable of obtaining the deflection angle "$\theta_t$" indicating the direction of the transmission and reception beam, by controlling ultrasound transmission and reception. Specifically, the controller 18 obtains the deflection angle "$\theta_t$" based on various transmission and reception conditions that have been set before ultrasonic scan.

In addition, the controller 18 obtains the angle "$\theta_0$" between the direction of the x axis and the direction of the boundary of the structure by various methods explained hereinafter. In the simplest method, the controller 18 obtains a value that is initially preset as the angle "$\theta_0$". For example, the controller 18 obtains a value "$\theta_0$=0" or "$\theta_0$=3" from a set value stored in the internal storage unit 17. In such a case, the operator can change the initial setting value of "$\theta_0$" to a desired value according to information such as the region to be examined.

Figure 11:
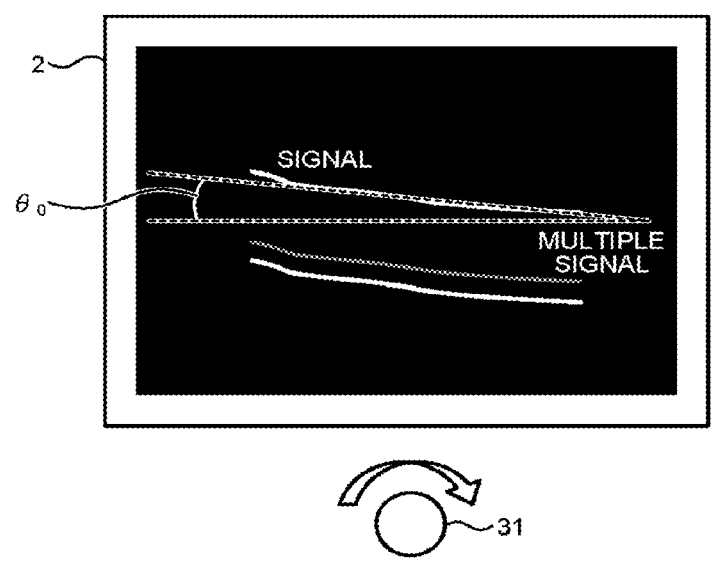
FIG. 11 is a diagram (1) for explaining a process to be performed by a controller according to the first embodiment.

As another example, the angle "$\theta_0$" indicating the direction of the structure is obtained using ultrasonic image data obtained by imaging the scan range to be subjected to actual ultrasonic scan by an ordinary B mode. In such a case, the controller 18 contains the direction indicating the boundary of the structure, based on information that is input by the operator who has referred to ultrasonic image data obtained in advance. For example, the controller 18 displays B mode image data obtained in advance by preliminary imaging on the monitor 2, as illustrated in FIG. 11. The B mode image data illustrated in FIG. 11 includes a drawn "signal" corresponding to an inclined blood vessel wall, and a drawn "multiple signal" corresponding to multiple reflection caused by a blood vessel wall in a shallow position. The B mode image data illustrated in FIG. 11 includes no drawn "multiple signal" corresponding to multiple reflection caused by a blood vessel wall in a deep position, due to attenuation or the display depth. The operator measures the inclination of the blood vessel wall in the shallow position that causes a multiple signal, using an angle measurement tool.

For example, the operator measures the angle of the "signal", by turning an angle measuring knob 31 included in the input device 3, as illustrated in FIG. 11. The controller 18 obtains the angle measured by the operator with the knob 31, as the angle "$\theta_0$" between the direction of the x axis and the direction indicating the boundary of the structure.

Figure 12:
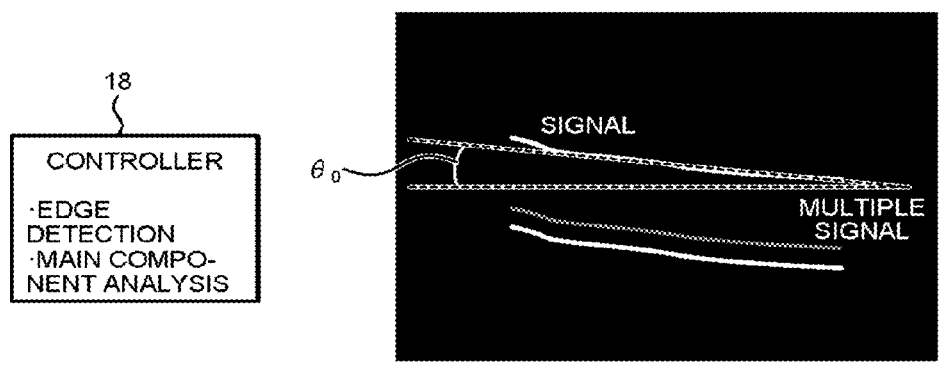
FIG. 12 is a diagram (2) for explaining the process to be performed by the controller according to the first embodiment.

Here, the controller 18 may automatically obtain the direction indicating the boundary of the structure, because manually measuring the direction indicating the boundary of the structure is processing that requires the operator's labor. When it is designated to automatically perform the processing of obtaining the angle "$\theta_0$", the controller 18 analyses ultrasonic image data obtained in advance, to estimate the direction indicating the boundary of the structure. Here, the controller 18 performs edge detection or main component analysis as processing of analyzing the ultrasonic image data obtained in advance, to estimate the angle "$\theta_0$" between the direction of the x axis and the direction of the boundary of the structure, as illustrated in FIG. 12. The B mode image data illustrated in FIG. 12 is the same image as the B mode image data illustrated in FIG. 11. For example, the controller 18 obtains a normal vector by performing edge emphasis processing on the B mode image data illustrated in FIG. 12, and detects the edge from the obtained normal vector. Thereafter, the controller 18 estimates the angle "$\theta_0$" from the direction of the detected edge. The above method is a mere example. The controller 18 can estimate the angle "$\theta_0$" by varieties of publicly known methods.

Here, when the detection of the angle "$\theta_0$" is performed by processing of detecting image information, the controller 18 may perform the following processing to reduce the load. Specifically, the controller 18 analyzes ultrasonic image data obtained in advance, in a region close to a predetermined depth. In other words, the controller 18 performs processing of detecting image information only on a region of interest (ROI) that is set in the B mode image data imaged in advance. For example, the ROI is set by the operator who has referred to the B mode image data.

As another example, the controller 18 may automatically set the ROI, to reduce the burden on the operator. For example, the controller 18 uses a depth located in the center of the image, as the predetermined depth used for automatic setting of the ROI. Generally, a region depicted in the center of the image is a region that is particularly noticed in image diagnosis. Accordingly, the controller 18 automatically set the ROI with the center of the image as the center, to avoid a multiple signal from being depicted in the center of the image.

As another example, the controller 18 uses the depth at which the tissue to be examined is located from the abutting surface of the ultrasonic probe 1, as the predetermined depth used for automatic setting of the ROI. For example, the controller 18 obtains information that the tissue to be examined is "carotid artery", from information that is input in advance and related to examination. Generally, the depth of the carotid artery from the abutting surface of the ultrasonic probe 1 is "10 mm" or around. For example, the internal storage unit 17 stores therein a table in which a typical depth of the position of the tissue is set for each of the tissues to be examined. The controller 18 obtains the depth associated with the tissue obtained from the examination information with reference to such a table, to set the ROI. As described above, the controller 18 automatically sets the ROI with the depth at which the tissue to be examined is located serving as the center, to avoid a multiple signal from being depicted in a region in which the tissue to be examined is depicted.

As another example, the controller 18 uses the position of the transmission focus, as the predetermined depth used for automatic setting of an ROI. The region including the position of the transmission focus as the center is also a region that is particularly noticed in image diagnosis. For this reason, the controller 18 automatically sets the ROI including the position of the depth of the transmission focus as the center, to avoid a multiple signal from being depicted in a region in which the tissue to be examined is depicted.

Next, the controller 18 according to the first embodiment calculates the reception position, without obtaining a depth "d" at which the structure is located on the scan line, as explained hereinafter. Specifically, in the first embodiment, the controller 18 calculates the reception position, on the assumption that the structure is located in each of depths of a plurality of reception focuses set on the reception scan line. This process will be explained hereinafter with reference to FIG. 13.

Figure 13:
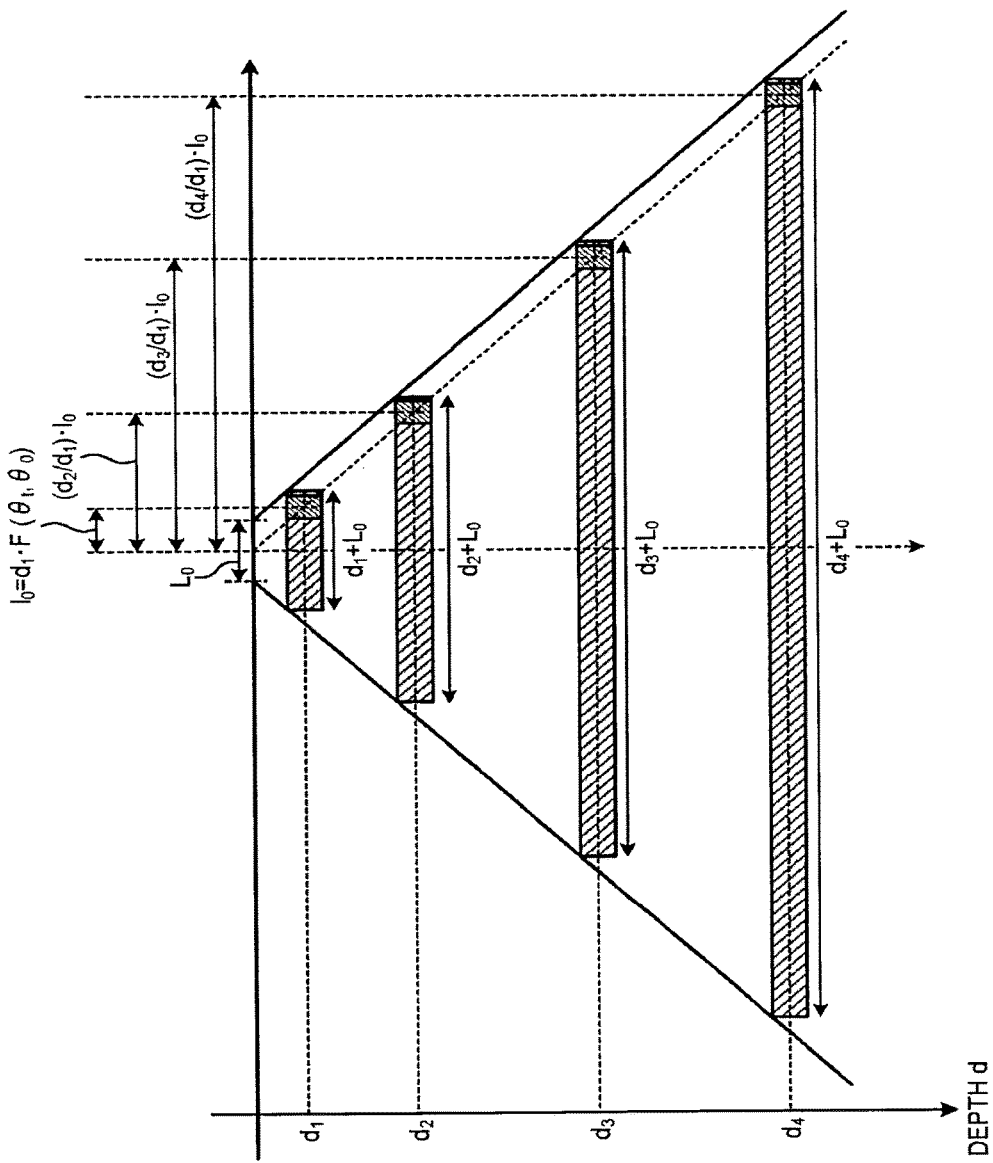
FIG. 13 is a diagram (3) for explaining the process to be performed by the controller according to the first embodiment.

For example, the controller 18 sets depths "$d_1, d_2, d_3, d_4 \ldots$" of reception focuses on the scan line as "d" used for calculation of the reception position, as illustrated in FIG. 13. The controller 18 performs control to change the width of the reception aperture in accordance with the position of the reception focus. Specifically, the controller 18 causes the reception unit 12 to perform DVAF described above. Thereafter, the controller 18 calculates the reception position to select at least one transducer element in the reception aperture of each reception focus. The controller 18 calculates the reception position in the reception aperture of each reception focus in each reception scan line.

FIG. 13 illustrates the reception aperture of each reception focus set by DVAF, and each reception aperture is disposed at the depth of the corresponding reception focus. The width (L) by which the aperture width of the reception aperture is enlarged is "L=d/F-number" based on the depth "d" of the reception focus and "F-number".

Here, the value "$L_0$" in FIG. 13 is an initial value of the aperture width that is provided at the depth "0". In FIG. 13, "F-number=1" is set. For this reason, the aperture width at the depth "$d_1$" is "$d_1+L_0$" as illustrated in FIG. 13. In the same manner, the aperture widths at the respective depths "$d_2, d_3, d_4$" are "$d_2+L_0, d_3+L_0, d_4+L_0$", respectively, as illustrated in FIG. 13. Because the reception aperture extends from the center of the aperture toward the both ends in DVAF, the inclination of the straight line that runs through the end point of the reception aperture is "F-number/2=½" in FIG. 13 in which the reception apertures of the respective reception focuses are arranged.

The controller 18 calculates the reception position "X=$l_0$" at the depth "$d_1$" by "$l_0$=$d_1$·F ($\theta_t$, $\theta_0$)", as illustrated in FIG. 13. The controller 18 also calculates the reception positions at the respective depths "$d_2$, $d_3$, $d_4$" as "($d_2/d_1$)·$l_0$, ($d_3/d_1$)·$l_0$, ($d_4/d_1$)·$l_0$", respectively, using the proportional relation, as illustrated in FIG. 13. FIG. 13 illustrates that a multiple reflection component (such as the main beam of multiple reflection) is received at a position on the right side of the central part of the reception aperture, due to the relation between the angle "$\theta_t$" and the angle "$\theta_0$".

The creating unit 124 creates an aperture function with a reduced weight for the range including the reception position, based on the reception position calculated by the controller 18 in the reception aperture of each reception focus, and notifies the phasing adder 125 of the aperture function.

Figure 14:
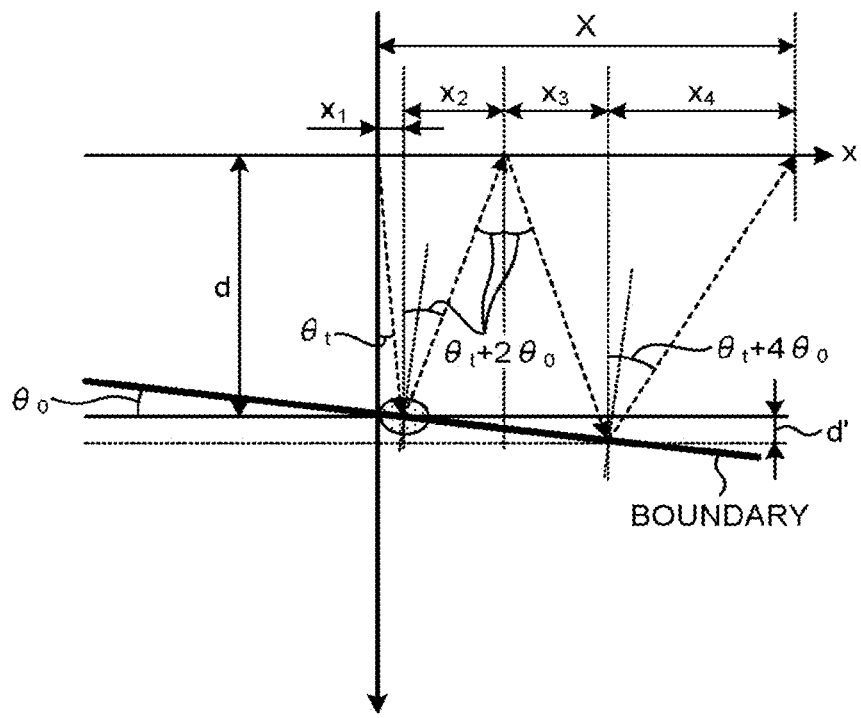
FIG. 14 is a diagram (4) for explaining the process to be performed by the controller according to the first embodiment.

Next, a method for calculating the reception position will be explained in detail hereinafter with reference to FIG. 14 to FIG. 16 and mathematical expressions. FIG. 14 illustrates that ($x_1$, d) is the position (hereinafter referred to as P1) where the ultrasonic beam transmitted at the angle "$\theta_t$" first reaches the boundary inclined at the angle "$\theta_0$". FIG. 14 also illustrates that ($x_1$+$x_2$, 0) is a position (hereinafter referred to as P2) where the reflected wave reflected at P1 is received on the probe surface by mirror reflection with the angle "$\theta_t$" and the angle "$\theta_0$". FIG. 14 also illustrates that ($x_1$+$x_2$+$x_3$, d+d') is a position (hereinafter referred to as P3) where the reflected wave reflected at P2 reaches the boundary again by mirror reflection with the angle "$\theta_t$" and the angle "$\theta_0$". FIG. 14 also illustrates that ($x_1$+$x_2$+$x_3$+$x_4$, 0) is a position (hereinafter referred to as P4) where the reflected wave reflected at P3 is received on the probe surface by mirror reflection with the angle "$\theta_t$" and the angle "$\theta_0$".

As illustrated in FIG. 14 and the following Expression (1), "$x_1$+$x_2$+$x_3$+$x_4$" is the position "X" illustrated in FIG. 10A and calculated by shift type reception apodization, that is, the position "X" of the center of gravity for the range occupied by the transducer elements with a weight of exactly or almost "0" in the aperture function.

$$X = x_1 + x_2 + x_3 + x_4 \quad (1)$$

First, the "angle made between the direction from the origin toward P1 and the depth direction" is "$\theta_t$", as illustrated in FIG. 14. In addition, the "angle made between a direction from P1 to P2 and the depth direction" and the "angle made between a direction from P2 to P3 and the depth direction" is "$\theta_t$+2$\theta_0$", as illustrated in FIG. 14, by geometrical calculation on the assumption that reflected with the angle "$\theta_t$" and the angle "$\theta_0$" is mirror reflection. The "angle made between a direction from P3 to P4 and the depth direction" is "$\theta_t$+4$\theta_0$", as illustrated in FIG. 14, by similar geometrical calculation.

First, the controller 18 calculates "$x_1$" by the following Expression (2), based on "$\theta_t$" and "d". The controller 18 also calculates "$x_2$" by the following Expression (3), based on "$\theta_t$+2$\theta_0$" and "d".

$$x_1 = d \cdot \tan(\theta_t) \quad (2)$$

$$x_2 = d \cdot \tan(\theta_t + 2\theta_0) \quad (3)$$

By contrast, "$x_3$" can be expressed with the following Expression (4), based on "$\theta_t$+2$\theta_0$", "d", and "d'". In addition, "$x_4$" can be expressed with the following Expression (5), based on "$\theta_t$+4$\theta_0$", "d", and "d'".

$$x_3 = (d + d') \cdot \tan(\theta_t + 2\theta_0) \quad (4)$$
$$= x_2 + d' \cdot \tan(\theta_t + 2\theta_0)$$

$$x_4 = (d + d') \cdot \tan(\theta_t + 4\theta_0) \quad (5)$$

In addition, "d'" can be expressed with the following Expression (6).

$$d' = (x_2 + x_3) \cdot \tan(\theta_0) \quad (6)$$
$$= (2x_2 + d' \cdot \tan(\theta_t + 2\theta_0)) \cdot \tan(\theta_0)$$

Here, Expression (6) is expanded to the following Expression (7).

$$d'(1 - \tan(\theta_t + 2\theta_0) \cdot \tan(\theta_0)) = 2x_2 \cdot \tan(\theta_0) \quad (7)$$

When an addition theorem of a trigonometric function in Expression (8) is used, the left side "1–tan($\theta_t$+2$\theta_0$)·tan ($\theta_0$)" of Expression (7) serves as the right side of the following Expression (9).

$$\tan(\alpha + \beta) = \frac{\tan\alpha + \tan\beta}{1 - \tan\alpha\tan\beta} \quad (8)$$

$$1 - \tan(\theta_t + 2\theta_0) \cdot \tan(\theta_0) = [\tan(\theta_t + 2\theta_0) + \tan(\theta_0)] / \tan(\theta_0 + 3\theta_0) \quad (9)$$

Substituting Expression (9) into Expression (7) indicates that "d'" can be calculated from "$x_2$", "$\theta_t$", and "$\theta_0$", as in the following Expression (10).

$$d' = 2x_2 \tan(\theta_0)\tan(\theta_t + 3\theta_0)/[\tan(\theta_t + 2\theta_0) + \tan(\theta_0)] \quad (10)$$

Based on the above, "$x_3$" can be calculated by the following Expression (11), and "$x_4$" can be calculated by the following Expression (12).

$$x_3 = (d + d') \cdot \tan(\theta_t + 2\theta_0) \quad (11)$$
$$= x_2 \cdot (1 + 2 \cdot \tan(\theta_t + 2\theta_0) \cdot \tan(\theta_0) \cdot \tan(\theta_t + 3\theta_0)/$$
$$[\tan(\theta_t + 2\theta_0) + \tan(\theta_0)])$$

$$x_4 = (d + d') \cdot \tan(\theta_t + 4\theta_0) \quad (12)$$
$$= x_2 \cdot (1 + 2 \cdot \tan(\theta_t + 4\theta_0) \cdot \tan(\theta_0) \cdot \tan(\theta_t + 3\theta_0)/$$
$$[\tan(\theta_t + 2\theta_0) + \tan(\theta_0)])$$

By the above method, the controller 18 obtains the angle "$\theta_t$" and the angle "$\theta_0$", and substitutes the depth "d" of the reception focus, to calculate "$x_1$" and "$x_2$" by Expressions (2) and (3). Thereafter, the controller 18 calculates "$x_3$" and "$x_4$" by Expression (11) and Expression (12) using the calculated "$x_2$", "$\theta_t$", and "$\theta_0$". The controller 18 thereafter calculates "$x_1$+$x_2$+$x_3$+$x_4$", to obtain the reception position "X". As is clear from Expression (2), Expression (3), Expression (11), and Expression (12), "X=$x_1$+$x_2$+$x_3$+$x_4$" can be formulated into the product of "d" and the function F ($\theta_t$, $\theta_0$) that is expressed with the angle "$\theta_t$" and the angle "$\theta_0$", when "d" is pulled out as a common factor. The controller 18 multiplies the value of any depth "d" by a value obtained by substituting the obtained angle "$\theta_t$" and the angle "$\theta_0$" into F ($\theta_t$, $\theta_0$), to calculate the reception position "X" in the reception aperture set for each reception focus, and select at least one transducer element located in the reception position "X".

Figure 15:
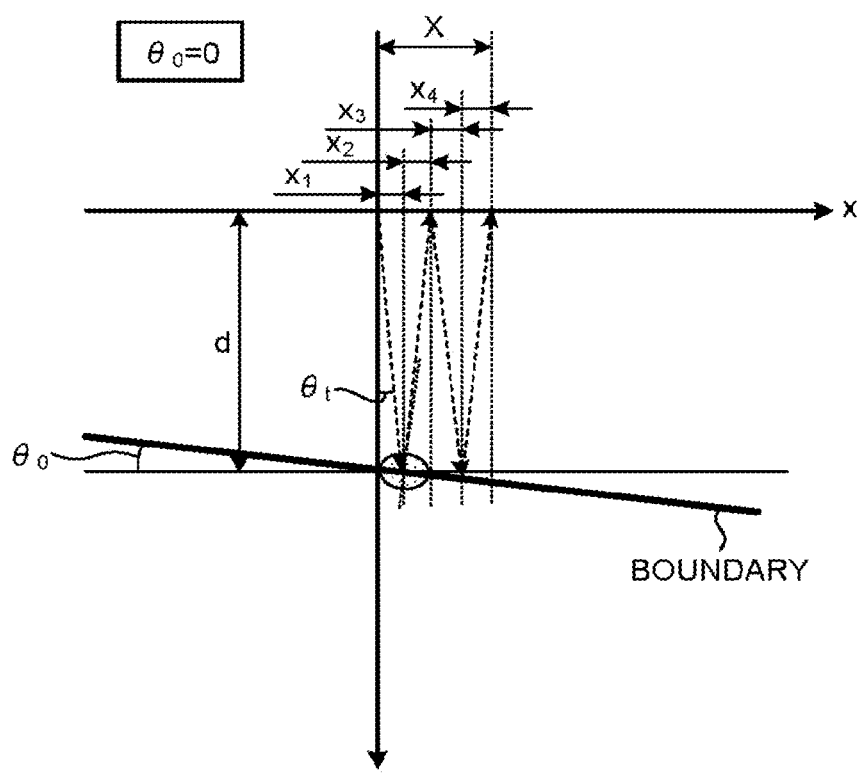
FIG. 15 is a diagram (5) for explaining the process to be performed by the controller according to the first embodiment.
Figure 16:
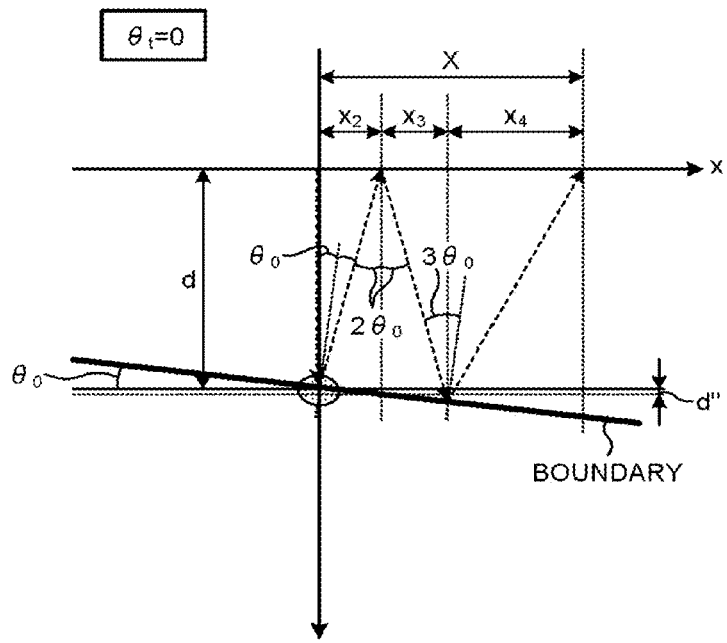
FIG. 16 is a diagram (6) for explaining the process to be performed by the controller according to the first embodiment.

The above calculation method can be simplified in the case illustrated in FIG. 15 or FIG. 16. FIG. 15 illustrates an example of the case where "X" is determined using F ($\theta_t$, 0) obtained by substituting "$\theta_0=0$" into F ($\theta_t$, $\theta_0$). The example illustrated in FIG. 15 illustrates the case where "X" is determined with "$\theta_0=0$", because "$\theta_0=0$" is set in the above initial setting, although actually the boundary formed of the structure is inclined in a direction of the angle "$\theta_0$." In other words, the example illustrated in FIG. 15 illustrates the case where shift type reception apodization is performed only with a deflection angle of ultrasonic wave serving as the first parameter, in an ultrasound test in which the boundary of the structure is assumed to be parallel with the x axis.

In such a case, all the "$x_1$", "$x_2$", "$x_3$", and "$x_4$" are "$d \cdot \tan(\theta_t)$", only based on the angle "$\theta_t$" at which the transmission beam is steered, as illustrated in the following Expression (13).

$$\left.\begin{aligned} x_1 &= d \cdot \tan(\theta_t) \\ x_2 &= d \cdot \tan(\theta_t) \\ x_3 &= d \cdot \tan(\theta_t) \\ x_4 &= d \cdot \tan(\theta_t) \end{aligned}\right\} \quad (13)$$

Specifically, the transmission beam that is steered at an angle "$\theta_t$" toward "$\theta_0=0$" serving as the direction of the structure is reflected at the position ($d \cdot \tan(\theta_t)$, d), and received at the position ($2d \cdot \tan(\theta_t)$, 0). In the case of a multiple reflection signal, the transmission beam is reflected again on the probe surface, and further reflected by the structure to be received. Consequently, the transmission beam is received at the position that is shifted from the central position (aperture central position) of the transmission beam by "$4d \cdot \tan(\theta_t)$".

Specifically, in the case where the initial setting is performed on the assumption "$\theta_0=0$", the controller 18 calculates the reception position "X" serving as the position of the center of gravity for the range with a reduced weight as "$4d \cdot \tan(\theta_t)$", by the following Expression (14).

$$X=4d \cdot \tan(\theta_t) \quad (14)$$

The controller 18 calculates the reception position "X" as "$X=4d \cdot \tan(\theta_t)$", also in the case where the measurement value obtained from the operator or the value obtained by image information detection processing is "$\theta_0=0$".

FIG. 16 illustrates an example of the case where "X" is determined using a value obtained by substituting "$\theta_t=0$" into F ($\theta_t$, $\theta_0$), because the transmission beam is not deflected. In the example illustrated in FIG. 16, the controller 18 obtains "$\theta_0$" from the initially set value, the measurement value obtained from the operator, or the value obtained by image information detection processing. In other words, the example illustrated in FIG. 16 illustrates the case where shift type reception apodization is performed only with the angle "$\theta_0$" that is made between the direction of the x axis and the boundary of the structure and serves as the second parameter or the third parameter, in an ultrasonic test in which ultrasound transmission and reception are performed without deflection.

FIG. 16 illustrates that ($x_1=0$, d) is the position (hereinafter referred to as P1') where the ultrasonic beam transmitted at the angle "$\theta_t=0$" first reaches the boundary inclined at the angle "$\theta_0$". FIG. 16 also illustrates that ($x_2$, 0) is a position (hereinafter referred to as P2') where the reflected wave reflected at P1' is received on the probe surface by mirror reflection. FIG. 16 also illustrates that ($x_3$, d+d") is a position (hereinafter referred to as P3') where the reflected wave reflected at P2' reaches the boundary again by mirror reflection. FIG. 14 also illustrates that ($x_2+x3+x_4$, 0) is a position (hereinafter referred to as P4') where the reflected wave reflected at P3' is received on the probe surface by mirror reflection.

In addition, the "angle made between a direction from P1' to P2' and the depth direction" and the "angle made between a direction from P2' to P3' and the depth direction" is "$2\theta_0$", as illustrated in FIG. 16. The "angle made between a direction from P3' to P4' and the depth direction" is "$4\theta_0$", as illustrated in FIG. 16.

The values "$x_1$", "$x_2$", "$x_3$", and "$x_4$" illustrated in FIG. 16 are expressed with the following Expression (15), by substituting "$\theta_t=0$" into Expressions (1) to (4).

$$\left.\begin{aligned} x_1 &= 0 \\ x_2 &= d \cdot \tan(2\theta_0) \\ x_3 &= (d+d'') \cdot \tan(2\theta_0) = x_2 + d'' \cdot \tan(2\theta_0) \\ x_4 &= (d+d'') \cdot \tan(4\theta_0) \end{aligned}\right\} \quad (15)$$

In addition, "d"" can be expressed with the following Expression (16).

$$\begin{aligned} d'' &= (x_2+x_3) \cdot \tan(\theta_0) \\ &= (2x_2 + d'' \cdot \tan(2\theta_0)) \cdot \tan(\theta_0) \end{aligned} \quad (16)$$

Expression (16) is expanded to the following Expression (17).

$$d''(1-\tan(\theta_0)\tan(2\theta_0))=2x_2 \cdot \tan(\theta_0) \quad (17)$$

When the addition theorem of the trigonometric function in Expression (8) is used, the following Expression (18) is obtained from Expression (17).

$$d''=x_2 \cdot 2 \tan(\theta_0)\tan(3\theta_0)/(\tan(2\theta_0)+\tan(\theta_0)) \quad (18)$$

Based on the above, "$x_3$" illustrated in FIG. 16 can be calculated by the following Expression (19), and "$x_4$" illustrated in FIG. 16 can be calculated by the following Expression (20).

$$\begin{aligned} x_3 &= (d+d'') \cdot \tan(2\theta_0) \\ &= x_2 \cdot (1 + 2 \cdot \tan(2\theta_0) \cdot \tan(\theta_0) \cdot \tan(3\theta_0)/ \\ &\quad [\tan(2\theta_0) + \tan(\theta_0)]) \end{aligned} \quad (19)$$

$$\begin{aligned} x_4 &= (d+d'') \cdot \tan(3\theta_0) \\ &= x_2 \cdot (1 + 2 \cdot \tan(4\theta_0) \cdot \tan(\theta_0) \cdot \tan(3\theta_0)/ \\ &\quad [\tan(2\theta_0) + \tan(\theta_0)]) \end{aligned} \quad (20)$$

In the case of "$\theta_t=0$", "X" can be calculated by the product of d and a function of "$\theta_0$", as expressed with Expression (15), Expression (19), and Expression (20).

By the calculation method explained above, the controller 18 calculates "X" in the reception aperture of each reception focus from the obtained angle "$\theta_t$" and the angle "$\theta_0$", to perform transducer element selection processing. Thereafter, the creating unit 124 creates an aperture function, for example, with a weight of "0" for a range "$X\alpha$ to $X\beta$" having "X" as the center of gravity in the reception aperture and a weight of "1" for a range outside the range "$X\alpha$ to $X\beta$"

in the reception aperture. For example, the controller 18 sets "Xα=X−dX" and "Xβ=X+dX". The value "dX" may be set in the system as initial setting, or may be set by the operator. However, the controller 18 performs setting such that the range having "X" as the center of gravity is located in the reception aperture, regardless of the value of "dX".

Figure 17:
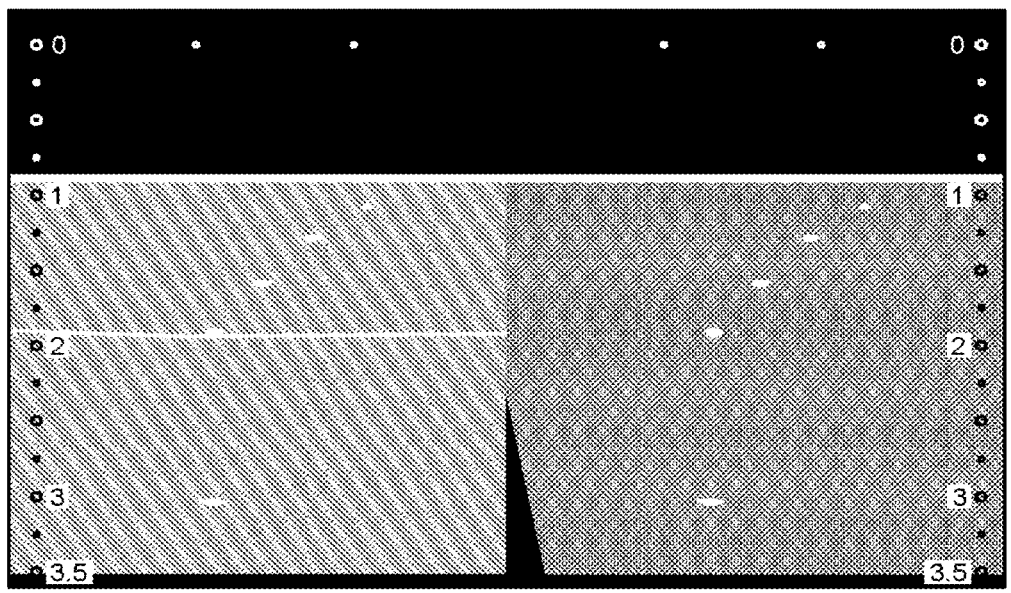
FIG. 17 is a diagram (1) for explaining an effect of the first embodiment.
Figure 18:
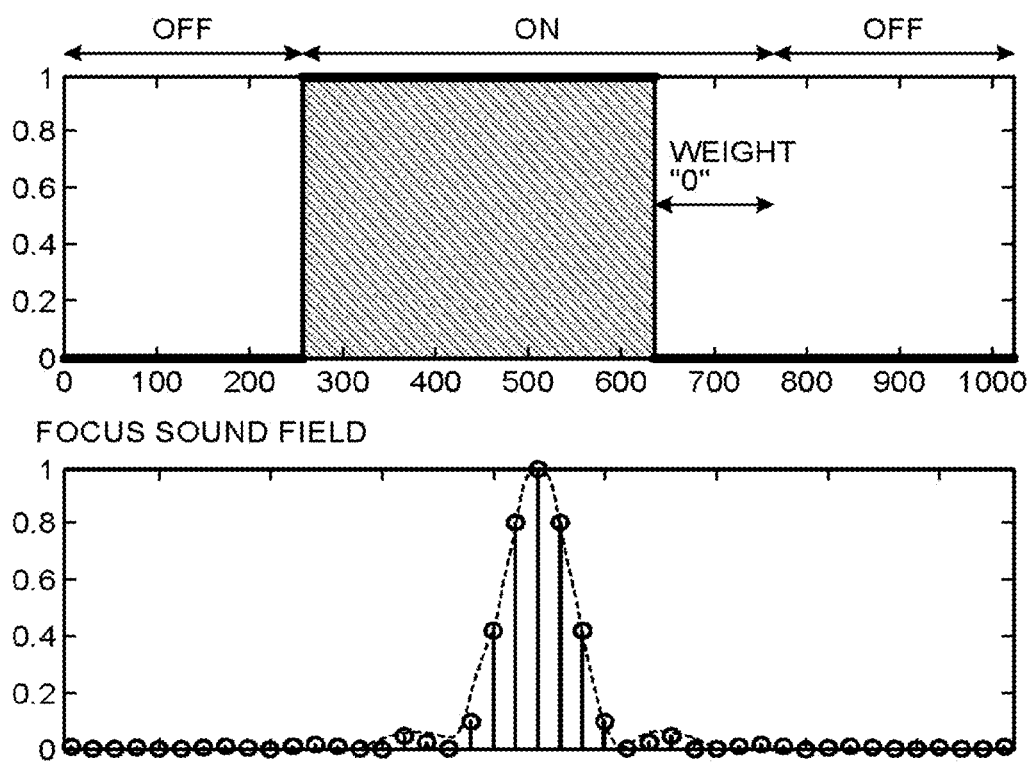
FIG. 18 is a diagram (2) for explaining the effect of the first embodiment.

The effect obtained by the above shift type reception apodization will be explained hereinafter with reference to FIG. 17 and FIG. 18. FIG. 17 and FIG. 18 are diagrams for explaining the effect of the first embodiment. FIG. 17 illustrates B mode image data obtained by ordinary B mode imaging on the left side, and B mode image data obtained by the above shift type reception apodization on the right side. The two images illustrated in FIG. 17 are obtained by imaging a phantom in which the boundary is horizontal ($\theta_0$=0 degree) to the probe surface and the boundary is disposed at a depth of "10 mm". In the phantom, wires are arranged in respective positions that are deeper than the depth "10 mm".

The B mode image data on the right side of FIG. 17 is an image obtained by performing shift type reception apodization with "X=4d·tan($\theta_t$)" under the conditions of the steering angle "$\theta_t$=10 degrees" and the angle "$\theta_0$=0 degree". As illustrated in FIG. 17, multiple reflection exists at the position at a depth of "20 mm" in the left B mode image data. By contrast, FIG. 17 demonstrates that a multiple signal is significantly reduced in the left B mode image data by using an aperture function the range with a weight of "0" is moved and set with "X=4d·tan($\theta_t$)".

In addition, comparison of the left and right images illustrated in FIG. 17 has revealed that deterioration in azimuth resolution occurring in the above premise method is reduced. Specifically, when the left and right images illustrated in FIG. 17 are compared, the width of each wire in the azimuth direction is substantially the same. This is considered to be caused by difference in sound field distribution around the focus between fixed type reception apodization and shift type reception apodization. This point will be explained hereinafter with reference to FIG. 18.

The upper drawing of FIG. 18 illustrates the positions of the transducer elements in the horizontal axis, and the weights of the aperture function in the vertical axis, in the same manner as the upper drawing of FIG. 8. The upper drawing of FIG. 18 also illustrates a range set as the reception aperture with "ON", and ranges that are not set as the reception aperture with "OFF", in the same manner as the upper drawing of FIG. 8. The upper drawing of FIG. 18 illustrates an aperture function with a weight "0" set for the right end part of the reception aperture, and a weight "1" set for the other range of the reception aperture, by the above shift type reception apodization.

The lower drawing of FIG. 18 illustrates a focus sound field obtained by performing Fourier transform on the aperture function illustrated in the upper drawing of FIG. 18. When the lower drawing of FIG. 18 is compared with the lower drawing of FIG. 8, they are different in sound field distribution around the focus. Specifically, the lower drawing of FIG. 18 illustrates that increase in the side-lobe with respect to the main-lobe is suppressed in comparison with the lower drawing of FIG. 8 by using an aperture function with a weight of "0" set for the right end part of the reception aperture.

For example, when the angle made between the direction of the angle "$\theta_t$" and the angle "$\theta_0$" is extremely large, the reception aperture becomes equivalent to a state where an aperture part of one side is removed, by the aperture function set by shift type reception apodization. This reduces the effective aperture width, although the aperture width is asymmetrical with respect to the transmission and reception scan line. In such a case, in the sound field distribution, the side-lobe component does not increase more than the method of providing the central aperture with a weight of "0", although azimuth resolution is slightly reduced due to spread of the side-lobe. Consequently, as illustrated in FIG. 17, shift type reception apodization enables suppression of deterioration in image quality in the azimuth direction that is significantly caused in the premise method.

Figure 19:
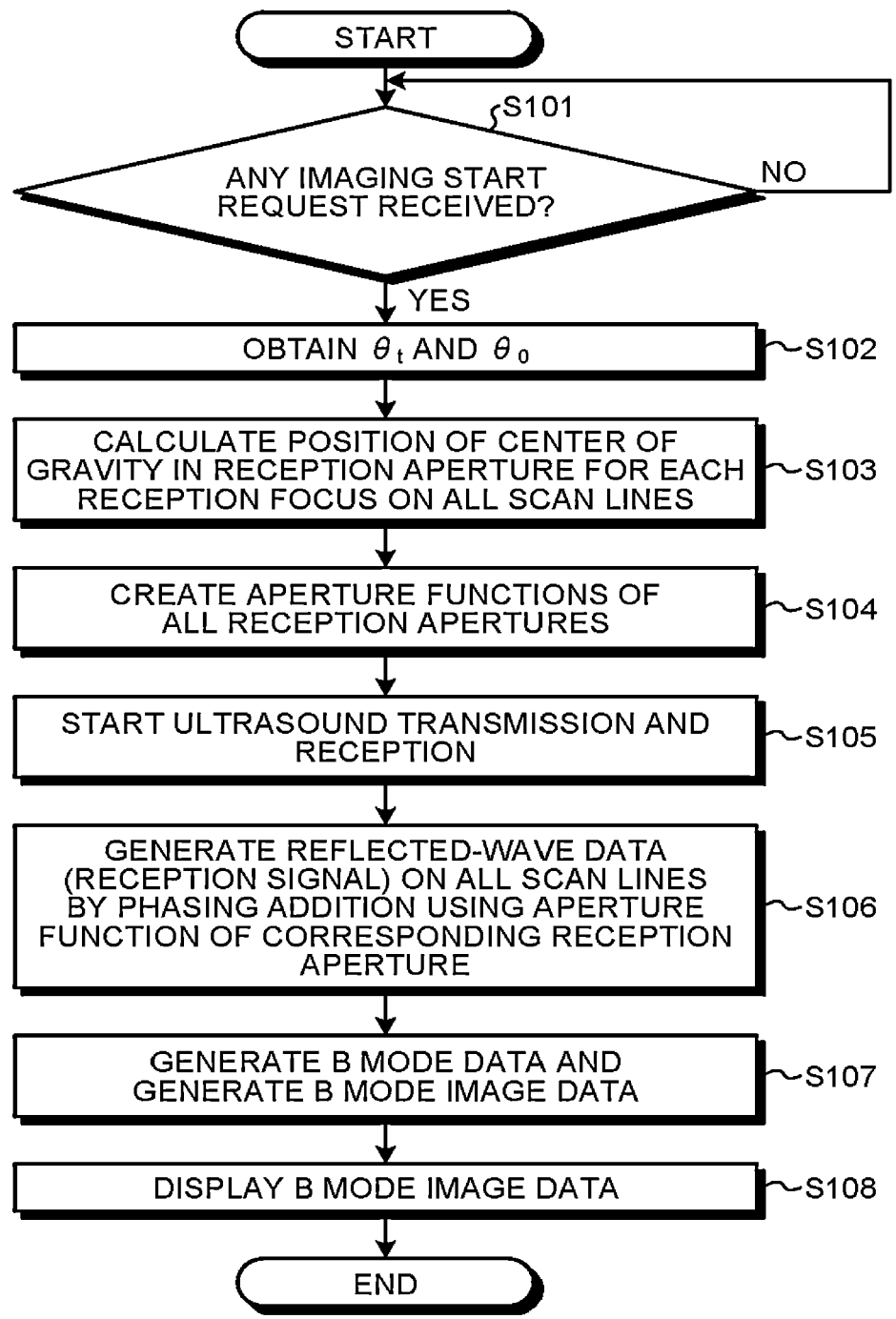
FIG. 19 is a flowchart illustrating an example of a process performed by the ultrasonic diagnosis apparatus according to the first embodiment.

The following is explanation of flow of a process performed by the ultrasonic diagnosis apparatus according to the first embodiment with reference to FIG. 19. FIG. 19 is a flowchart illustrating an example of a process performed by the ultrasonic diagnosis apparatus according to the first embodiment. FIG. 19 illustrates an example of a process performed using a preset value as the angle "$\theta_0$".

As illustrated in FIG. 19, the controller 18 of the ultrasonic diagnosis apparatus according to the first embodiment determines whether an imaging start request with shift type reception apodization is received (step S101). When no imaging start request is received (No at step S101), the controller 18 waits until it receives an imaging start request.

On the other hand, when an imaging start request is received (Yes at step S101), the controller 18 obtains $\theta_t$ and $\theta_0$ (step S102). Next, the controller 18 calculates a position (X) of the center of gravity in the reception aperture for each reception focus on all the scan lines (step S103). Thereafter, the controller 18 performs selection processing based on the calculated position of the center of gravity, to set a reduction range. Next, the creating unit 124 creates aperture functions of all the reception apertures, in accordance with an instruction from the controller 18 (step S104).

Thereafter, the controller 18 starts ultrasound transmission and reception (step S105). In this manner, digital data of a reflection signal subjected to reception delay processing are successively input to the phasing adder 125. Next, the phasing adder 125 generates reflected-wave data for a frame, that is, reflected-wave data (reception signal) on all the scan lines (reception scan lines) by phasing addition using an aperture function of the corresponding reception aperture (step S106). Next, the B mode processor 13 generates B mode data, and the image generator 15 generates B mode image data (step S107).

Next, under the control of the controller 18, the monitor 2 displays the B mode image data (step S108), and the controller 18 ends the process. The process from step S106 to step S108 is repeated until an imaging end request is received. According to the first embodiment, the operator who has referred to B mode image data may correct at least one value of $\theta_t$ and $\theta_0$, and imaging with shift type reception apodization may be performed again under the corrected condition.

As described above, according to the first embodiment, the position at which the main beam of multiple reflection is received in the reception aperture is calculated based on mirror reflection that occurs according to the direction of ultrasound transmission and reception and the direction indicating the boundary of the structure, and an aperture function with a reduced weight for a certain range having the calculated position as the center of gravity is set. Consequently, the first embodiment enables acquisition of B mode data with reduced multiple reflection, without being influenced by inclination of the transmission and reception beam or inclination of the structure.

In addition, according to the first embodiment, because the reception position is calculated with each reception focus position on the reception scan line that is set as the depth of the structure, the range with a reduced weight can be simply set.

The operator may move the position of the ultrasonic probe 1, for example, while the process from step S106 to step S108 illustrated in FIG. 19 is repeated. In such a case, the controller 18 selects at least one transducer element whenever the ultrasonic probe 1 is moved, to cause the reception unit 12 to perform shift type reception apodization processing (reduction processing) according to the selected transducer element. As a result, the first embodiment enables reduction in multiple reflection of each ultrasonic image data generated by successive imaging.

Second Embodiment

Figure 20:
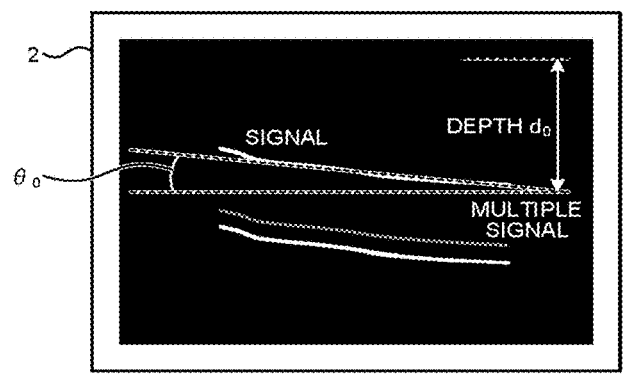
FIG. 20 is a diagram (1) for explaining a second embodiment.
Figure 20:
Figure 21:
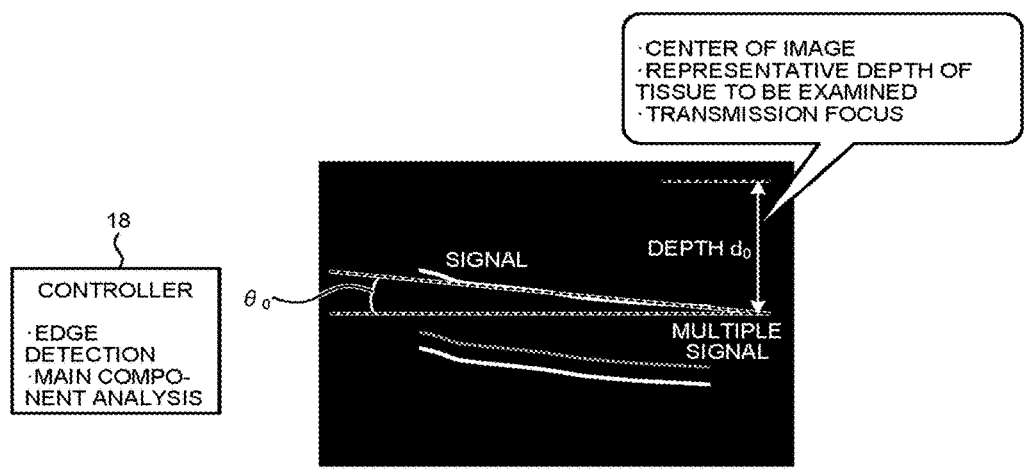
FIG. 21 is a diagram (2) for explaining the second embodiment.
Figure 22:
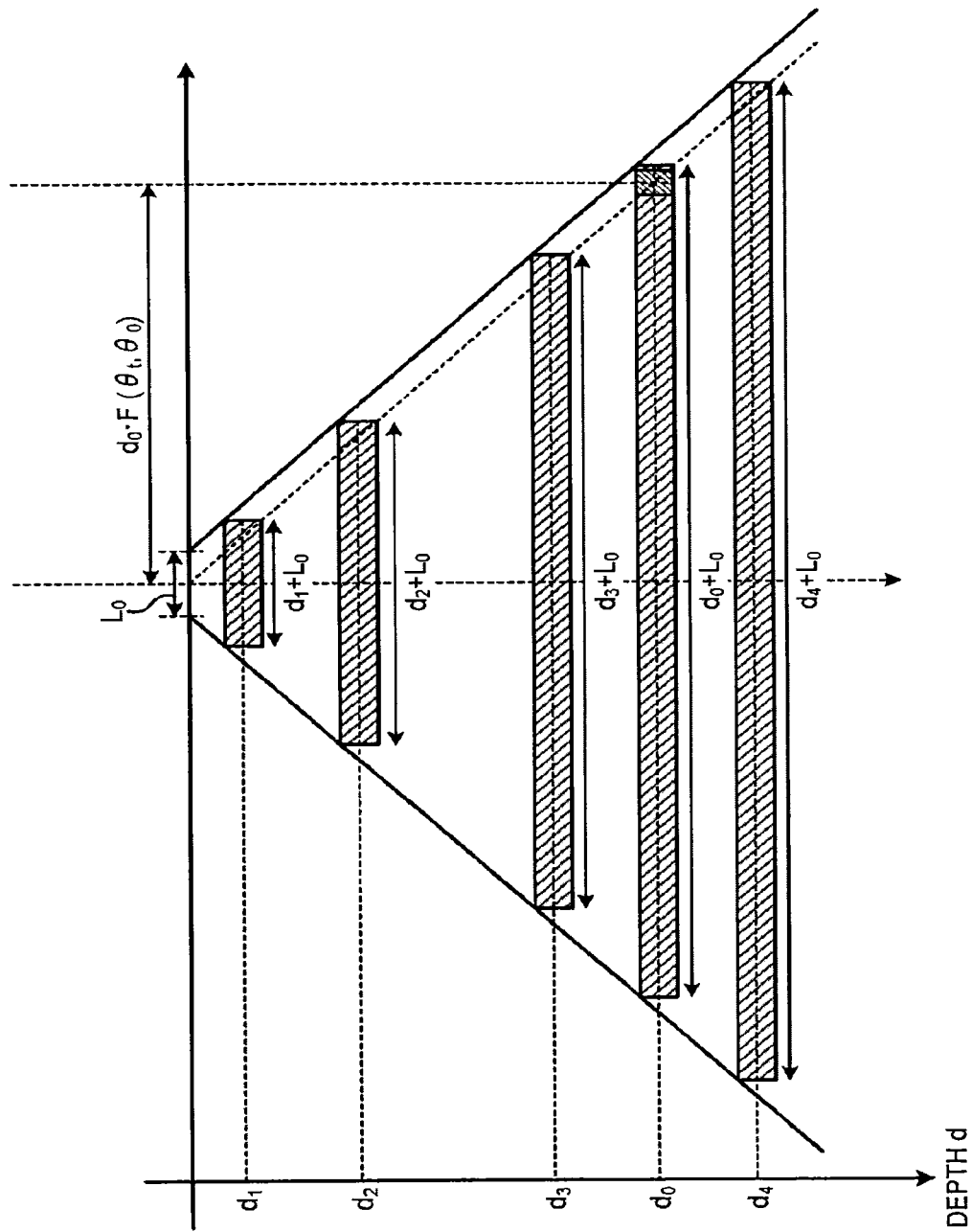
FIG. 22 is a diagram (3) for explaining the second embodiment.

The second embodiment illustrates the case of performing shift type reception apodization by obtaining a depth of the structure as well as the direction (deflection angle of the ultrasonic wave) of ultrasound transmission and reception and the direction indicating the boundary of the structure, with respect to FIG. 20 to FIG. 22. FIG. 20 to FIG. 22 are diagrams for explaining the second embodiment.

The ultrasonic diagnosis apparatus according to the second embodiment is constructed in the same manner as the ultrasonic diagnosis apparatus according to the first embodiment illustrated in FIG. 1. In addition, the reception unit 12 according to the second embodiment is constructed in the same manner as the reception unit 12 according to the first embodiment illustrated in FIG. 2. The controller 18 according to the second embodiment performs control to change the width of the reception aperture according to the position of the reception focus, in the same manner as the first embodiment. Specifically, the controller 18 causes the reception unit 12 to execute DVAF.

However, the controller 18 according to the second embodiment selects "at least one transducer element" in the reception aperture of the reception focus corresponding to the depth of the structure. Specifically, the controller 18 calculates the reception position in the reception aperture of the reception focus corresponding to the depth of the structure, to select transducer element selection processing. In the first embodiment, the depth itself of the structure is not used as an input parameter. Instead, in the first embodiment, the depth of the structure is set to the reception focus position, and the position of "X" is automatically calculated with F ($\theta_r$, $\theta_0$) and "F-number". However, in the first embodiment, because transducer elements with a weight of "0" always exist at each depth "d" as illustrated in FIG. 13, the effective aperture width is always smaller than that of ordinary reception apodization. As a result, the first embodiment has the possibility that the image quality of B mode image data is reduced.

For this reason, in the second embodiment, the depth (hereinafter referred to as "$d_0$") of the structure is obtained, and shift type reception apodization is performed only with "$d_0$".

Here, the controller 18 obtains the depth "$d_0$" of the structure, based on information that is set by the operator who has referred to the "ultrasonic image data (B mode image data) obtained in advance" explained in the first embodiment. Specifically, the controller 18 according to the second embodiment obtains the direction indicating the boundary of the structure and the depth of the structure, based on information that is input by the operator who has referred to ultrasonic image data obtained in advance. The B mode image data displayed on the monitor 2 and illustrated in FIG. 20 is the same as the B mode image data illustrated in FIG. 11. In the same manner as the first embodiment, the operator turns the knob 31 to measure the angle of the "signal", as illustrated in FIG. 20. The controller 18 obtains the angle measured by the operator with the knob 31 as an angle "$\theta_0$" indicating the direction of the structure.

Moreover, the operator simultaneously measures the depth "$d_0$", as illustrated in FIG. 20. The controller 18 obtains the depth measured by the operator as the depth "$d_0$" of the structure.

As another example, the controller obtains the depth "$d_0$", based on a result of detection of image information of the "ultrasonic image data (B mode image data) obtained in advance", to reduce the burden on the operator. Specifically, the controller 18 analyses the ultrasonic image data obtained in advance, to estimate the direction indicating the boundary of the structure and the depth of the structure. More specifically, the controller 18 estimates the angle "$\theta_0$" by edge detection and main component analysis, as explained in FIG. 12. The second embodiment also enables setting an ROI based on varieties of predetermined depth explained in the first embodiment, and perform image information detection processing only in the ROI.

Here, for example, when the edge extracted by edge detection is regarded as the boundary formed of the structure, the controller 18 is capable of obtaining a rough position of the boundary in the image from the image information. Accordingly, the controller 18 is capable of obtaining the depth "$d_0$" by automatically measuring the position of the edge in the image. As described above, the controller 18 according to the second embodiment is capable of obtaining the depth "$d_0$" of the structure, together with the angle "$\theta_0$" indicating the direction of the structure, by processing of detecting image information.

As another example, the controller 18 may obtain the depth of the structure based on preset information. Specifically, the controller 18 may use varieties of information (predetermined depth) used for setting the ROI explained in the first embodiment, as "$d_0$" without any processing. More specifically, the controller 18 estimate the angle "$\theta_0$" by edge detection or main component analysis, as illustrated in FIG. 21. Next, the controller 18 obtains the "center of the image", "representative depth of the tissue to be examined", or "transmission focus" used for setting the ROI as "$d_0$", as illustrated in FIG. 21. Setting "transmission focus=$d_0$" enables instantaneous correspondence to change of the transmission and reception conditions during imaging.

FIG. 22 illustrates reception apertures at the respective reception focuses "$d_1$, $d_2$, $d_3$, $d_4$ . . . " set under the same conditions as those of DVAF illustrated in FIG. 13. FIG. 22 illustrates the case where the depth "$d_0$" of the structure obtained any of the above three methods is located between "$d_3$" and "$d_4$". In such a case, the controller 18 sets "$d_0$" as a new reception focus, as illustrated in FIG. 22. The reception aperture width at the depth "$d_0$" is "$d_0+L_0$" based on "F-number=1", as illustrated in FIG. 22.

Next, the controller 18 calculates the reception position "$d_0 \cdot F(\theta_r, \theta_0)$" only with the depth "$d_0$", as illustrated in FIG. 22. Thereafter, the creating unit 124 creates an aperture function, for example, with a weight of "0" for the range having "$d_0 \cdot F(\theta_r, \theta_0)$" as the center of gravity for the reception focus "$d_0$". The creating unit 124 according to the second embodiment creates aperture functions used in ordinary reception apodization for reception focuses other than the reception focus "$d_0$". Such aperture functions may be "aperture functions of a rectangular window", "aperture functions as a Hanning window", or "aperture functions of a flat-top window", as well as "aperture functions of a Hamming window".

The phasing adder 125 weights the signals that have been subjected to reception delay processing and obtained at the reception aperture of the reception focus "$d_0$" with an aperture function to set a weight of "0" for the range (reduction range) including "$d_0 \cdot F (\theta_r, \theta_0)$" as a basis (such as the center of gravity), and add the signals. In this manner, the phasing adder 125 obtains a reception signal for a plurality of sample points near the reception focus "$d_0$". The controller 18 may perform the following processing because the depth "$d_0$" of the structure is obtained as the depth of the structure on a certain line. For example, the controller 18 specifies a region that may be occupied by the structure in the scan range, based on the position of the scan line at which the depth "$d_0$" of the structure is obtained and the inclination "$\theta_0$" of the structure. Next, for example, the controller 18 performs adjustment such that most of a plurality of sample points on all the scan lines near the reception focus "$d_0$" are located within the region. This adjustment enables the controller 18 to effectively reduce the multiple component. As another example, the controller 18 may determine the depth of the structure on each scan line, and may perform shift type reception apodization only for the depth determined in each scan line.

In addition, the phasing adder 125 weights signals that have been obtained in the reception apertures of the reception focuses other than the reception focus "$d_0$" and subjected to reception delay processing with ordinary aperture functions, and adds the signals. In this manner, the phasing adder 125 obtains a reception signal of all the sample points other than the reception focus "$d_0$". In this manner, the phasing adder 125 obtains a reception signal (reflected-wave data) on the reception scan line.

The details explained in the first embodiment are applicable to the second embodiment, except for the point of performing shift type reception apodization only in the reception aperture having the depth "$d_0$" of the structure as the reception focus. However, the shift type reception apodization explained in the first embodiment may be performed by adding the depth "$d_0$" of the structure obtained by the controller 18 to the reception focus.

Figure 23:
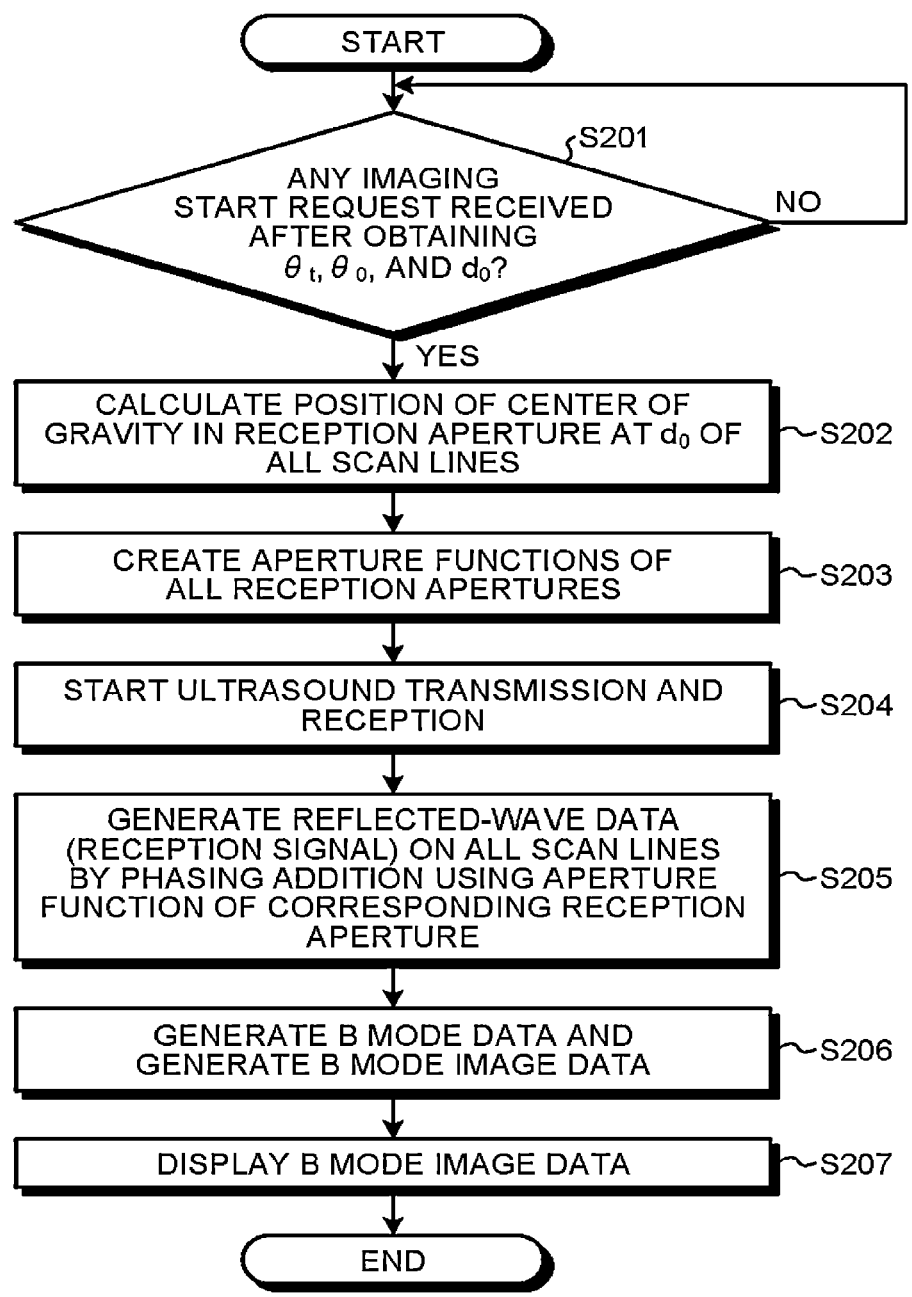
FIG. 23 is a flowchart illustrating an example of a process performed by an ultrasonic diagnosis apparatus according to the second embodiment.

The following is explanation of a flow of a process performed by the ultrasonic diagnosis apparatus according to the second embodiment, with reference to FIG. 23. FIG. 23 is a flowchart illustrating an example of a process performed by the ultrasonic diagnosis apparatus according to the second embodiment.

As illustrated in FIG. 23, the controller 18 of the ultrasonic diagnosis apparatus according to the second embodiment determines whether an imaging start request with shift type reception apodization is received after obtaining $\theta_r$, $\theta_0$, and do (step S201). When no imaging start request is received (No at step S201), the controller 18 waits until it receives an imaging start request.

On the other hand, when an imaging start request is received (Yes at step S201), the controller 18 calculates a position (X) of the center of gravity in the reception aperture at do on all the scan lines (step S202). Thereafter, the controller 18 performs selection processing based on the calculated position of the center of gravity, to set a reduction range. Next, the creating unit 124 creates aperture functions of all the reception apertures, in accordance with an instruction from the controller 18 (step S203). For example, the creating unit 124 creates an aperture function with a weight of "0" for the range having "$d_0 \cdot F (\theta_r, \theta_0)$" as the center of gravity for the reception focus "$d_0$", and creates aperture functions used in ordinary reception apodization for reception focuses other than the reception focus "$d_0$".

Thereafter, the controller 18 starts ultrasound transmission and reception (step S204). In this manner, digital data of a reflection signal subjected to reception delay processing are successively input to the phasing adder 125. Next, the phasing adder 125 generates reflected-wave data for a frame, that is, reflected-wave data (reception signal) on all the scan lines (reception scan lines) by phasing addition using an aperture function of the corresponding reception aperture (step S205). Next, the B mode processor 13 generates B mode data, and the image generator 15 generates B mode image data (step S206).

Next, under the control of the controller 18, the monitor 2 displays the B mode image data (step S207), and the controller 18 ends the process. The process from step S205 to step S207 is repeated until an imaging end request is received. According to the second embodiment, the operator who has referred to B mode image data may correct at least one value of $\theta_r$, $\theta_0$, and $d_0$, and imaging with shift type reception apodization may be performed again under the corrected condition.

As described above, according to the second embodiment, shift type reception apodization only with the depth of the structure is performed. Consequently, the second embodiment enables acquisition of B mode data with a reduced multiple signal, while reduction in image quality is prevented. As described above, the details explained in the first embodiment are applicable to the second embodiment. For example, also in the second embodiment, the controller 18 selects at least one transducer element whenever the ultrasonic probe 1 is moved, to cause the reception unit 12 to perform shift type reception apodization processing (reduction processing) according to the selected transducer element. As a result, the second embodiment enables reduction in multiple reflection of each ultrasonic image data generated by successive imaging.

Third Embodiment

Figure 24:
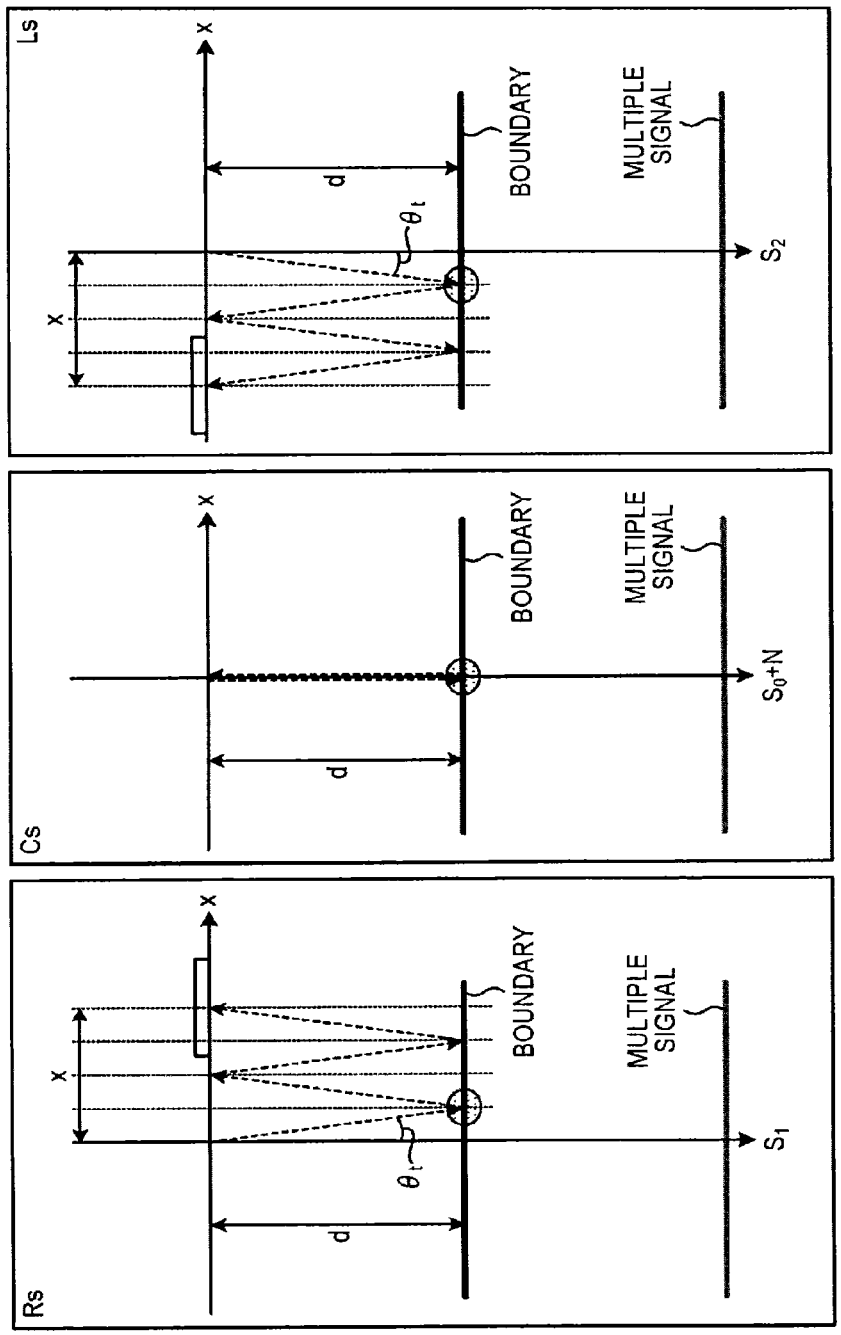
FIG. 24 is a diagram (1) for explaining a third embodiment.
Figure 25:
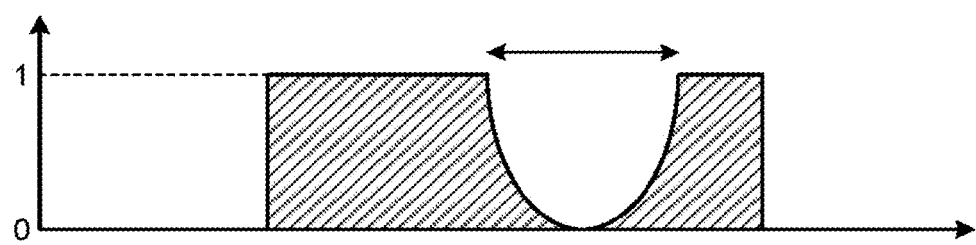
FIG. 25 is a diagram (1) for explaining a modification.

The third embodiment provides explanation of a method that is applicable to shift type reception apodization explained in the first embodiment and the second embodiment, to further improve the image quality of B mode image data, with reference to FIG. 24 and FIG. 25. FIG. 24 and FIG. 25 are diagrams for explaining the third embodiment.

For example, with reference to the B mode image data on the left side of FIG. 7 and the B mode image data on the left side of FIG. 17, the wires are obliquely depicted, when the transmission and reception beam is steered with the deflection angle "$\theta_t$". For this reason, the third embodiment solves the above problem by performing spatial compounding explained as conventional art, under the control of the controller 18. In addition, in the third embodiment, shift type reception apodization is applied to spatial compounding for deflecting the transmission beam, under the control of the controller 18. With the application, the third embodiment enables acquisition of B mode image data with reduced multiple reflection and an improved S/N ratio. The following is detailed explanation of a process performed in the third embodiment.

First, the controller 18 according to the third embodiment performs control to perform ultrasound scan a plurality of times with deflection angles of ultrasound transmission and reception that are different between frames. FIG. 24 illustrates the case where the boundary formed of the structure is parallel with the probe surface (x axis), that is, "$\theta_0=0$". For example, the controller 18 executes ultrasonic transmission and reception inclined with the angle "$\theta_t$" to the right, as illustrated in the left drawing of FIG. 24. The ultrasonic scan inclined with the angle "$\theta_t$" to the right is referred to as "Rs" hereinafter. Next, the controller 18 executes ultrasound transmission and reception inclined with an angle "0 degrees", that is, "$\theta_t=0$", as illustrated in the middle drawing of FIG. 24. The ultrasonic scan with "$\theta_t=0$" is referred to as "Cs" hereinafter. The controller 18 also executes ultrasound transmission and reception inclined with the angle "$\theta_t$" to the left, as illustrated in the right drawing of FIG. 24. The ultrasonic scan inclined with the angle "$\theta_t$" to the left is referred to as "Ls" hereinafter.

Next, the controller 18 according to the third embodiment select "at least one transducer element" in at least one ultrasonic scan. Specifically, the controller 18 calculates a reception position "X" in at least one ultrasonic scan. For example, the controller 18 calculates the reception position "X" in the ultrasonic scan "Rs" and the ultrasonic scan "Ls", as illustrated in FIG. 24. "$X=4d\cdot\tan(\theta_t)$" is satisfied, because "$\theta_0=0$". However, in the ultrasonic scan "Rs", the reception position is a position that is distant by "X" from the scan line to the right, as illustrated in the left drawing of FIG. 24. In the ultrasonic scan "Ls", the reception position is a position that is distant by "X" from the scan line to the left, as illustrated in the right drawing of FIG. 24.

Thereafter, the reception unit 12 serving as a processor according to the third embodiment executes processing (reduction processing) explained in the first embodiment and the second embodiment to output a reception signal of the reception aperture, in ultrasonic scan in which "at least one transducer element" is selected by the controller 18. The reception unit 12 executes processing that is different from the processing (reduction processing) to output a reception signal of the reception aperture, in ultrasonic scan in which "at least one transducer element" is not selected by the controller 18. The processing that is different from the reduction processing is, for example, phasing addition using an ordinary aperture function such as "aperture function of a Hamming window".

For example, in accordance with an instruction from the controller 18, the creating unit 124 creates an aperture function with a weight of "0" for the range having a position that is distant by "X" from the scan line to the right as the center of gravity, in the ultrasonic scan "Rs" (see the left drawing of FIG. 24). In addition, in accordance with an instruction from the controller 18, the creating unit 124 creates an aperture function with a weight of "0" for the range having a position that is distant by "X" from the scan line to the left as the center of gravity, in the ultrasonic scan "Ls" (see the right drawing of FIG. 24). In accordance with an instruction from the controller 18, the creating unit 124 creates an ordinary aperture function in the ultrasonic scan "Cs".

In this manner, in the ultrasonic scan "Rs" and "Ls", a "reception signal provided with an aperture function for multiple reflection reduction" is output from the phasing adder 125 to the B mode processor 13 and the image generator 15. In addition, in the ultrasonic scan "Cs", a "reception signal provided with an ordinary aperture function" is output from the phasing adder 125 to the B mode processor 13 and the image generator 15. In the example illustrated in FIG. 24, when shift type reception apodization is applied to the ultrasonic scan "Cs", a multiple component cannot be removed, and azimuth resolution deteriorates, because an aperture function similar to that in fixed type reception apodization is created. For this reason, in the case of "$\theta_0=0$", it is preferable not to apply shift type reception apodization to ultrasonic scan "Cs".

In the third embodiment, in ultrasonic scan "Rs" and "Ls", aperture functions for multiple reflection reduction may be created in reception apertures of all the reception focuses using the depth of each reception focus as explained in the first embodiment, or an aperture function for multiple reflection reduction may be created only in the reception aperture of the reception focus corresponding to the depth of the structure as explained in the second embodiment. When the third embodiment is applied to the second embodiment, for example, "$\theta_0$, $d_0$" is set in the controller 18 by the operator who has referred to B mode image data that was imaged in advance, before ultrasonic scan for spatial compounding is performed.

The image generator 15 according to the third embodiment generates ultrasonic image data of each ultrasonic scan, based on the reception signal of the reception aperture that is output by the reception unit 12 in each ultrasonic scan, and generates image data (image data having been subjected to arithmetic mean) obtained by combining a plurality of pieces of generated ultrasonic image data, as ultrasonic image data (display B mode image data).

Spatial compounding as conventional art is a method for reducing multiple artifacts in the image, by maintaining a signal component (that is, a true signal component derived from the tissue) with a relatively small change in intensity even when inclined by compound processing (arithmetic mean processing), using the fact that the position where a multiple reflection echo (noise) appears changed according to the deflection angle when the deflection angle of the ultrasonic beam is changed.

By contrast, according to the third embodiment, an aperture function for multiple reflection reduction based on the reception position is used in "Rs" and "Ls" using the deflection angle "$\theta_t$" under the condition "$\theta_0=0$", to obtain a reception signal with a reduced multiple reflection signal, as illustrated in FIG. 24. The left drawing of FIG. 24 illustrates a reception signal obtained by "Rs" as a signal $S_1$ in which noise of multiple reflection is almost removed. The right drawing of FIG. 24 illustrates a reception signal obtained by "Ls" as a signal $S_2$ in which noise of multiple reflection is almost removed.

Because "$\theta_0=0$" is satisfied in the example illustrated in FIG. 24, an ordinary aperture function is used in "Cs" for the reason described above. For this reason, the middle drawing of FIG. 24 illustrates a reception signal obtained by "Cs" as "$S_0+N$" obtained by adding the signal $S_0$ and multiple reflection noise N.

In conventional spatial compounding, multiple reflection noise is included in both the reception signal obtained by "L" and the reception signal obtained by "R". By contrast, in the third embodiment, the reception signal S that is consequently obtained by arithmetic mean processing is simply "$S=\{S_1+(S_0+N)+S_2\}/3=(S_1+S_0+S_2)/3+N/3$". Supposing that "$S'=(S_1+S_0+S_2)/3$", the reception signal S satisfies "$S=S'+N/3$". Specifically, "N" is reduced to "N/3", that is, the multiple reflection reduction effect is achieved by applying the shift type reception apodization explained in the first embodiment or the second embodiment to spatial compounding.

Although the above example illustrates the case where the ultrasonic scan "Cs" is performed as ordinary scan, shift type reception apodization may be applied also to ultrasonic scan "Cs". In such a case, the multiple reflection reduction effect is further increased, although azimuth resolution deteriorates due to the image data of "Cs". In addition, when the structure is actually inclined, shift type reception apodization may be performed in all the ultrasonic scans. The multiple reflection reduction effect can be obtained also in such a case. The operator may determine whether to perform shift type reception apodization in all the ultrasonic scans or perform shift type reception apodization in part of the ultrasonic scans, or the controller 18 may determine it based on relative relation between the value of "$\theta_0$" and the steering angle used for spatial compounding.

As described above, the third embodiment enables acquisition of B mode image data with a further reduced multiple signal, while preventing reduction in image quality, by applying shift type reception apodization to spatial compounding.

In the third embodiment, ultrasonic scan is performed a plurality of times with deflection angles of ultrasound transmission and reception that are different between frames. For example, in the above example, three ultrasonic scans are performed to output composite image data for a frame. In the third embodiment, although composite image data for a frame may be output whenever ultrasonic scans for a set are performed, the frame rate decreases in such a case. For this reason, the controller 18 performs the following process to maintain the frame rate. For example, suppose that the B mode image data generated in the first set are "R (1), C (1), L (1)". In addition, suppose that the B mode image data generated in the second set are "R (2), C (2), L (2)".

The image generator 15 performs arithmetic mean on "R (1), C (1), L (1)" under the control of the controller 18, to generate composite image data for the first frame. The image generator 15 also performs arithmetic mean on "C (1), L (1), R (2)" under the control of the controller 18, to generate composite image data for the second frame. The image generator 15 also performs arithmetic mean on "L (1), R (2), C (2)" under the control of the controller 18, to generate composite image data for the third frame. The image generator 15 also performs arithmetic mean on "R (2), C (2), L (2)" under the control of the controller 18, to generate composite image data for the fourth frame. This control can prevent the frame rate from decreasing in the third embodiment. The controller 18 selects at least one transducer element whenever the ultrasonic probe 1 is moved, even in the case of performing continuous imaging in which shift type reception apodization is applied to spatial compounding. As a result, the third embodiment also enables reduction in multiple reflection of each ultrasonic image data generated by continuous imaging.

The image processing methods explained in the above first to third embodiments illustrate the cases of creating an aperture function only for the reception position of one-time multiplexing. However, in the image processing methods explained in the above first to third embodiments, aperture functions may be created also for two-time multiplexing and three-time multiplexing. However, because the reception position may be located outside the reception aperture or the intensity of the multiple reflection signal is reduced due to attenuation in two-time multiplexing and three-time multiplexing, it is preferable to create an aperture function limited to the reception position of one-time multiplexing, to simplify the process.

Figure 26:
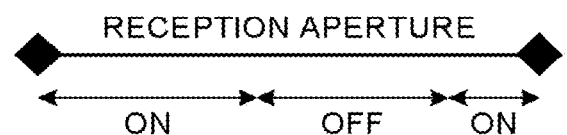
FIG. 26 is a diagram (2) for explaining a modification.

In addition, the image processing methods explained in the above first to third embodiments illustrate the cases of reducing multiple reflection using an aperture function with a weight of "0" for the range including the reception position "X". However, in the first to third embodiments, a modification illustrated in FIG. 25 or FIG. 26 may be performed as the method for reducing multiple reflection using the reception position "X". FIG. 25 and FIG. 26 are diagrams for explaining modifications.

Specifically, in shift type reception apodization, the effect of reducing multiple reflection can be achieved with an aperture function in which a weight for the range (reduction range) including the reception position is reduced to be lower than a weight outside the range (outside the reduction range). For example, the creating unit 124 may create an aperture function illustrated in FIG. 25, in accordance with an instruction from the controller 18. The aperture function illustrated in FIG. 25 has a U shape in which both end positions of a weight of a range indicated by arrows have a weight of "1", the weight gradually reduces from the both ends toward the reception position, and the weight at the reception position is "0". Multiple reflection can be reduced also by using the aperture function illustrated in FIG. 25. As another example, the creating unit 124 may perform reduction processing on a reception signal that occurs in a transducer element other than the at least one transducer element selected by the controller 18, not a reception signal that occurs in a transducer element in the reduction range including at least one transducer element selected by the controller 18. For example, the creating unit 124 may create an aperture function with a weight of "1" for the reduction range and a weight that is larger than "1" outside the reduction range, to relatively reduce the weight for the reduction range.

In addition, the controller 18 may shut off an output from the range (reduction range) including at least one transducer element, and use a reception signal based on the output signal from outside the range (outside the reduction range), as the reception signal of the reception aperture. For example, the controller 18 shuts off an output from the transducer elements in a range including the reception position "X" in the reception aperture, as illustrated in FIG. 26 (see "OFF" in the drawing). For example, the controller 18 also sets the outputs from transducer elements outside the range to "ON" in the reception aperture, as illustrated in FIG. 26. The phasing adder 125 performs phasing addition on output signals from transducer elements outside the range, to generate a reception signal of the reception aperture illustrated in FIG. 26. Also in this manner, multiple reflection can be reduced.

The above explanation illustrates the cases where the image processing methods explained in the first to third embodiments and the modification are performed in an ultrasonic diagnosis apparatus. However, the image processing methods explained in the first to third embodiments and the modification may be performed in an image processing apparatus that is capable of obtaining a signal received by the ultrasonic probe 1.

In addition, it is noted that the components of each device illustrated in the description of the foregoing embodiments are functional concepts and may not necessarily be physically configured as illustrated in the drawings. That is, specific manners of distribution and integration of the devices are not limited to those illustrated in the drawings and the whole or part thereof may be distributed or integrated functionally or physically in any units depending on various loads and use conditions. For example, the processing (reduction processing) explained in the above embodiments may be separately installed in the ultrasonic diagnosis apparatus as a processor other than the reception unit 12. The whole or any part of the processing functions in each device may be implemented by a CPU and a computer program that is analyzed and executed by the CPU, or may be implemented by hardware with wired logic.

The image processing method described in the first to third embodiments and the modification can be implemented by executing an image processing program prepared in advance by a computer such as a personal computer and a workstation. The image processing program can be distributed over networks such as the Internet. Otherwise, the image processing program may be recorded on a non-transitory computer-readable recording medium such as a hard disk, a flexible disk (FD), a compact disc read only memory (CD-ROM), a magneto-optical disc (MO), a digital versatile disc (DVD), and a flash memory such as a universal serial bus (USB) memory and an SD card memory, and read out from the non-transitory recording medium by a computer for execution.

At least one of the embodiments described above can reduce multiple reflection.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnosis apparatus comprising:
   a transducer element group formed of a plurality of transducer elements arranged linearly in a predetermined direction;
   a receiver configured to generate reception signals representing amplitudes of an ultrasonic wave at the plurality of transducer elements;
   a transmitter configured to transmit, into a subject, the ultrasonic wave in a transmit direction that is at a deflection angle; and
   processing circuitry configured to
      estimate, by analyzing a previously obtained ultrasonic image, a first direction that is orthogonal to a boundary of a structure in the subject,
      select at least one transducer element in a reception aperture formed of the transducer element group, the at least one transducer element being selected to be associated with a multiple reflection of the ultrasonic wave from the boundary of the structure, and the at least one transducer element being selected based on (i) a first angle representing a difference between the first direction and a second direction, which is orthogonal to the predetermined direction in which the transducer elements are linearly arranged, and (ii) the deflection angle at which the ultrasonic wave is transmitted,
      obtain a plurality of reception signals including a first reception signal generated in the selected at least one transducer element and second reception signals generated in other transducer elements, which are in the transducer element group forming the reception aperture other than the selected at least one transducer element,
      apply weights to the plurality of reception signals, the weights reducing the first reception signal more than the second reception signals to generate a weighted plurality of reception signals, and
      generate another ultrasonic image based on the weighted plurality of reception signals.

2. The ultrasonic diagnosis apparatus according to claim 1, wherein the processing circuitry is further configured to create an aperture function including the weights applied to the plurality of reception signals, in which a weight applied to the selected at least one transducer element reduces the first reception signal more than the second reception signals, and
   the applying of the weights and generating the another ultrasonic image are performed by weighting the reception signals generated by the respective transducer elements forming the reception aperture using the aperture function and subjecting the weighted plurality of reception signals to phasing addition to generate the another ultrasonic image.

3. The ultrasonic diagnosis apparatus according to claim 2, wherein the processing circuitry is further configured to create the aperture function by setting the weight applied to the receptions signals of the selected at least one transducer element to zero.

4. The ultrasonic diagnosis apparatus according to claim 1, wherein the processing circuitry is further configured to exclude from the another ultrasonic image output from a range including the at least one transducer element, and uses a reception signal based on an output signal excluding the range as a reception signal of the reception aperture.

5. The ultrasonic diagnosis apparatus according to claim 1, wherein the processing circuitry is further configured to change a width of the reception aperture in accordance with a position of a reception focus, and
   select, for the reception aperture having the changed width, the at least one transducer element, wherein
   the selecting of the at least one transducer element is performed for each reception focus.

6. The ultrasonic diagnosis apparatus according to claim 1, wherein the processing circuitry is further configured to change a width of the reception aperture in accordance with a position of a reception focus, and
   select, for the reception aperture having the changed width, the at least one transducer element, wherein
   the reception aperture corresponding to the reception focus depends on a depth of the structure.

7. The ultrasonic diagnosis apparatus according to claim 6, wherein the processing circuitry is further configured to obtain the depth of the structure, based on information that is set by an operator who has referred to the ultrasonic image data obtained in advance, a result of detecting image information of the ultrasonic image data, or preset information.

8. The ultrasonic diagnosis apparatus according to claim 1, wherein processing circuitry is further configured to
   control the transducer element group, the receiver, and the transmitter to execute ultrasonic scans at respective times of a plurality of times, in each of the ultrasonic scans a different deflection angle of ultrasound transmission and reception being used for the respective ultrasonic scan, and the at least one transducer element being selected in at least one of the ultrasonic scans,
   output the plurality of reception signals reception signals of the reception aperture in the at least one of the ultrasonic scans, in which the at least one transducer element is selected, and
   perform phasing addition processing to the weighted plurality of reception signals of the at least one of the ultrasonic scans, and
   generate respective ultrasonic images corresponding to the respective ultrasonic scans, each ultrasonic image of each ultrasonic scan being based on the reception signals of the reception aperture of the corresponding ultrasonic scan.

9. The ultrasonic diagnosis apparatus according to claim 1, wherein the processing circuitry is further configured to estimate first direction using input by an operator who has access to the previously obtained ultrasonic image.

10. The ultrasonic diagnosis apparatus according to claim 1, wherein the processing circuitry is further configured to analyze the previously obtained ultrasonic image to estimate a depth of the structure.

11. The ultrasonic diagnosis apparatus according to claim 10, wherein the processing circuitry is further configured to analyze the previously obtained ultrasonic image in a region around a predetermined depth.

12. The ultrasonic diagnosis apparatus according to claim 11, wherein the processing circuitry is further configured to use a depth located in a center of an image, a depth at which a tissue to be examined is located from an abutting surface of an ultrasonic probe, or a position of a transmission focus, as the predetermined depth.

13. The ultrasonic diagnosis apparatus according to claim 1, wherein the processing circuitry is further configured to select the at least one transducer element whenever an ultrasonic probe moves.

14. An ultrasonic diagnosis apparatus comprising:
a transducer element group formed of a plurality of transducer elements arranged in a predetermined direction which is a direction along an arc having a predetermined curvature;
a receiver configured to generate reception signals representing amplitudes of an ultrasonic wave at the plurality of transducer elements;
a transmitter configured to transmit, into a subject, the ultrasonic wave in a transmit direction that is at a deflection angle; and
processing circuitry configured to
estimate, by analyzing a previously obtained ultrasonic image, a first direction that is orthogonal to a boundary of a structure in the subject,
determine a second direction that is perpendicular to a normal direction, the normal direction being normal to the transducer element group, which is arranged in along the arc having the predetermined curvature, at a center of the transducer element group,
select at least one transducer element in a reception aperture formed of the transducer element group, the at least one transducer element being selected to be associated with a multiple reflection of the ultrasonic wave from the boundary of the structure, and the at least one transducer element being selected based on (i) a first angle made between the determined second direction and the estimated first direction, and (ii) the deflection angle at which the ultrasonic wave is transmitted,
obtain a plurality of reception signals including a first reception signal generated in the selected at least one transducer element and second reception signals generated in transducer other elements, which are in the transducer element group forming the reception aperture other than the selected at least one transducer element,
apply weights to the plurality of reception signals, the weights reducing the first reception signal more than the second reception signals to generate a weighted plurality of reception signals, and
generate another ultrasonic image based on the weighted plurality of reception signals.

15. The ultrasonic diagnosis apparatus according to claim 14, wherein the processing circuitry is further configured to
change a width of the reception aperture in accordance with a position of a reception focus, and
select, for the reception aperture having the changed width, the at least one transducer element, wherein
the reception aperture corresponding to the reception focus depends on a depth of the structure.

16. The ultrasonic diagnosis apparatus according to claim 14, wherein the processing circuitry is further configured to estimate the first direction using input by an operator who has access to the previously obtained ultrasonic image.

17. The ultrasonic diagnosis apparatus according to claim 14, wherein the processing circuitry is further configured to analyze the previously obtained ultrasonic image to estimate a depth of the structure.

18. The ultrasonic diagnosis apparatus according to claim 17, wherein the processing circuitry is further configured to analyze the previously obtained ultrasonic image in a region around a predetermined depth.

19. The ultrasonic diagnosis apparatus according to claim 18, wherein the processing circuitry is further configured to use a depth located in a center of an image, a depth at which a tissue to be examined is located from an abutting surface of an ultrasonic probe, or a position of a transmission focus, as the predetermined depth.

20. An image processing method comprising:
performing an ultrasonic scan using
a transducer element group formed of a plurality of transducer elements arranged linearly in a predetermined direction,
a receiver configured to generate reception signals representing amplitudes of an ultrasonic wave at the plurality of transducer elements, and
a transmitter configured to transmit, into a subject, the ultrasonic wave in a transmit direction that is at a deflection angle;
estimating, by analyzing a previously obtained ultrasonic image a first direction that is orthogonal to a boundary of a structure in the subject;
selecting, using processing circuitry, at least one transducer element in a reception aperture formed of the transducer element group, the at least one transducer element being selected to be associated with a multiple reflection of the ultrasonic wave from the boundary of the structure, and the at least one transducer element being selected based on (i) a first angle representing a difference between the first direction and a second direction, which is orthogonal to the predetermined direction in which the transducer elements are linearly arranged, and (ii) the deflection angle at which the ultrasonic wave is transmitted;
obtaining a plurality of reception signals including a first reception signal generated in the selected at least one transducer element and second reception signals generated in other transducer elements, which are in the transducer element group forming the reception aperture other than the selected at least one transducer element;
applying, using the processing circuitry, weights to the plurality of reception signals, the weights reducing the first reception signal more than the second reception signals to generate a weighted plurality of reception signals; and generating, using the processing circuitry, another ultrasonic image based on the weighted plurality of reception signals.

21. An image processing method comprising:
performing an ultrasonic scan using
   a transducer element group formed of a plurality of transducer elements arranged in a predetermined direction along an arc having a predetermined curvature,
   a receiver configured to generate reception signals representing amplitudes of an ultrasonic wave at the plurality of transducer elements, and
estimating, using processing circuitry, a first direction that is orthogonal to a boundary of a structure in the subject by analyzing a previously obtained ultrasonic image;
determining, using the processing circuitry, a second direction that is perpendicular to a normal direction, the normal direction being normal to the transducer element group, which is arranged in along the arc having the predetermined curvature, at a center of the transducer element group;
selecting, using the processing circuitry at least one transducer element in a reception aperture formed of the transducer element group, the at least one transducer element being selected to be associated with a multiple reflection of the ultrasonic wave from the boundary of the structure, and the at least one transducer element being selected based on (i) an angle made between the determined second direction and the estimated second direction, and (ii) the deflection angle at which the ultrasonic wave is transmitted;
obtaining a plurality of reception signals including a first reception signal generated in the at least one transducer element and second reception signals generated in other transducer elements, which are in the transducer element group forming the reception aperture other than the selected at least one transducer element;
applying, using the processing circuitry, weights to the plurality of reception signals, the weights reducing the first reception signal more than the second reception signals to generate a weighted plurality of reception signals; and
generating, using the processing circuitry, another ultrasonic image based on the weighted plurality of reception signals.

* * * * *